United States Patent [19]
Brittelli et al.

[11] 4,419,517
[45] Dec. 6, 1983

[54] 4A-ARYL-TRANS-DECAHYDROISOQUINO-LINES

[75] Inventors: David R. Brittelli, Nottingham, Pa.; William C. Ripka, Wilmington, Del.

[73] Assignee: E. I. Du Pont de Nemours & Co., Wilmington, Del.

[21] Appl. No.: 566,089

[22] Filed: Apr. 8, 1975

Related U.S. Application Data

[63] Continuation-in-part of Ser. No. 365,843, Jun. 1, 1973, abandoned, which is a continuation-in-part of Ser. No. 273,806, Jul. 20, 1972, abandoned.

[51] Int. Cl.$^3$ ............................................. C07D 217/14
[52] U.S. Cl. ...................................... 546/144; 424/258
[58] Field of Search ................... 424/258; 260/287 D, 260/288 D, 289 D; 546/144

[56] References Cited

U.S. PATENT DOCUMENTS

| | | | |
|---|---|---|---|
| 2,740,788 | 4/1956 | Grüssner et al. | 260/289 R |
| 3,546,227 | 12/1970 | Gmünder et al. | 260/288 R |
| 3,666,763 | 5/1973 | Grethe et al. | 260/289 R |
| 3,743,638 | 7/1973 | Webster | 260/281 R |
| 4,001,247 | 1/1977 | Zimmerman et al. | 260/289 D |
| 4,001,248 | 1/1977 | Zimmerman et al. | 260/287 D |
| 4,001,248 | 1/1977 | Zimmerman et al. | 260/289 D |
| 4,029,796 | 6/1977 | Zimmerman et al. | 424/258 |
| 4,077,954 | 3/1978 | Ripka | 424/258 |
| 4,100,166 | 7/1978 | Zimmerman et al. | 546/144 |
| 4,150,135 | 4/1979 | Ripka | 546/144 |
| 4,208,524 | 6/1980 | Zimmerman et al. | 546/144 |
| 4,219,652 | 8/1980 | Zimmerman et al. | 546/144 |
| 4,236,009 | 11/1980 | Zimmerman et al. | 546/144 |
| 4,289,882 | 9/1981 | Rapoport et al. | 546/144 |

FOREIGN PATENT DOCUMENTS 1164192 8/1966 United Kingdom ......... 260/283 SY

OTHER PUBLICATIONS

Boekelheide et al. "J.A.C.S.," 72, 712 (1950).
Eddy "J. of the Am. Pharm. Assoc." 1950, pp. 245 ff.

Primary Examiner—Mary C. Lee

[57] ABSTRACT

Certain 4a-aryl-trans-decahydroisoquinolines are useful as analgesics. Exemplary is N-cyclopropylmethyl-4a-m-hydroxyphenyl-trans-decahydroisoquinoline.

22 Claims, No Drawings

4A-ARYL-TRANS-DECAHYDROISOQUINOLINES

RELATED APPLICATION

This application is a continuation-in-part of patent application Ser. No. 365,843 filed June 1, 1973, now abandoned which is a continuation-in-part of patent application Ser. No. 273,806 filed July 20, 1972, now abandoned.

BACKGROUND OF THE INVENTION

1. Field of the Invention

The invention relates to certain novel 4a-aryl-trans-decahydroisoquinolines useful as analgesics and to processes for their manufacture.

2. Prior Art

N-methyl-4a-phenyl-cis-decahydroisoquinoline has been reported by Boekelheide and Schilling [J. Am. Chem. Soc. 72, 712 (1950)]. They named the compound "N-methyl-10-phenyldecahydroisoquinoline" and stated it has low analgesic activity.

DESCRIPTION OF THE INVENTION

The invention is a compound having the formula I

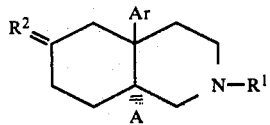

wherein $R^1$ is hydrogen, $C_1$-$C_6$ alkyl, benzyl (—$CH_2C_6H_5$), phenethyl (—$CH_2CH_2C_6H_5$), or cycloalkylmethyl of the formula —$CH_2CH<(CH_2)_n$ in which n is an integer in the range 2-5, $R^2$ is divalent oxygen (=O),

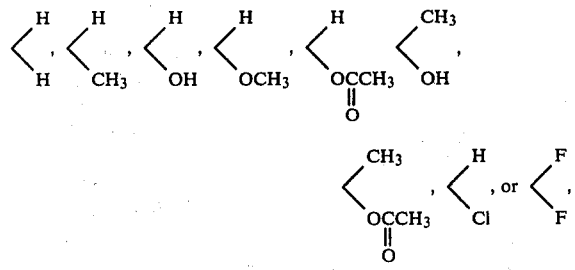

A is hydrogen or hydroxyl;
Ar is

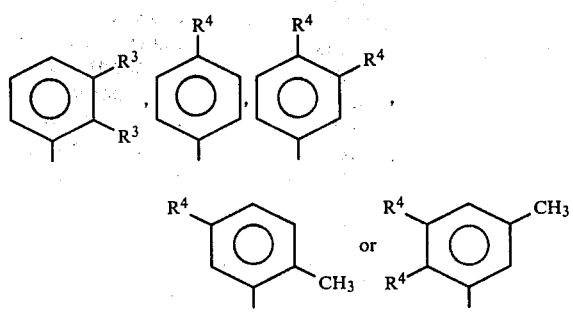

in which $R^3$, alike or different, is hydrogen, hydroxyl, methoxyl or acetoxyl;

$R^4$, alike or different, is hydroxyl, methoxyl or acetoxyl; and, jointly, two of $R^3$ or of $R^4$ situated on adjacent carbons may be combined to form a divalent methylenedioxy (—$OCH_2O$—) group.

Representative $R^1$ groups are methyl, ethyl, propyl, butyl, hexyl, cyclopropylmethyl [—$CH_2CH<(CH_2)_2$], cyclobutylmethyl [—$CH_2CH<(CH_2)_3$], and cyclohexylmethyl [—$CH_2CH<(CH_2)_5$].

Representative Ar groups are phenyl, 3-hydroxyphenyl, 3-methoxyphenyl, 4-methoxyphenyl, 2-acetoxyphenyl, 2,3-dihydroxyphenyl, 3,4-dimethoxyphenyl, 3,4-diacetoxyphenyl, 2-methyl-5-hydroxyphenyl, 3-methyl-5,6-dimethoxyphenyl, 3-hydroxy-4-methoxyphenyl, 2-methoxy-3-acetoxyphenyl, and 3,4-(methylenedioxy)phenyl.

The 4a-aryl-trans-decahydroisoquinolines of formula I include various stereochemical isomers stemming from substitution at position 6 and from optical asymmetry of the whole structure. At position 6, when monovalent $R^2$ substituents are different (e.g., when $R^2$ is

spatial considerations require the existence of axial and equatorial isomers. In the molecule as a whole, spatial considerations require the existence of d and l optical isomers. The latter are normally present as racemic mixtures which can be resolved by known methods (Eliel, Stereochemistry of Carbon Compounds, McGraw-Hill, 1962, p. 31). Intermediates can be resolved and converted to the corresponding optically active products.

The multi-step processes of the invention start with 2-cyano-3-aryl-3-carbalkoxymethylcyclohexenes that can be obtained according to procedures disclosed by Boekelheide and Schilling (loc. cit.) with respect to 2-cyano-3-phenyl-3-carbethoxymethylcyclohexene (cf, Example 1, Part A). A key step in these processes is the novel reaction of a 2-cyano-3-aryl-3-carbalkoxymethylcyclohexene with hydrogen chloride in a lower alkanol such as ethanol to form a 4a-aryl-1,3-diketo-1,2,3,4,4a,5,6,7-octahydroisoquinoline (cf, Example 1, Part B). The novel 1,3-diketo-1,2,3,4,4a,5,6,7-octahydroisoquinolines possess a conformational arrangement of the fused rings which requires formation of trans-decahydroisoquinoline structures when the 8,8a-double bond is converted to a single bond.

The selection of specific preparational steps following the initial formation of a 1,3-diketo-1,2,3,4,4a,5,6,7-octahydroisoquinoline depends upon the specific 4a-aryl-trans-decahydroisoquinoline derivative that is desired. The sequence involves at least three steps which can be illustrated as follows:

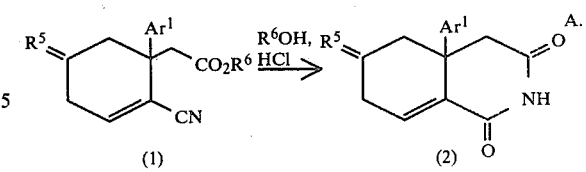

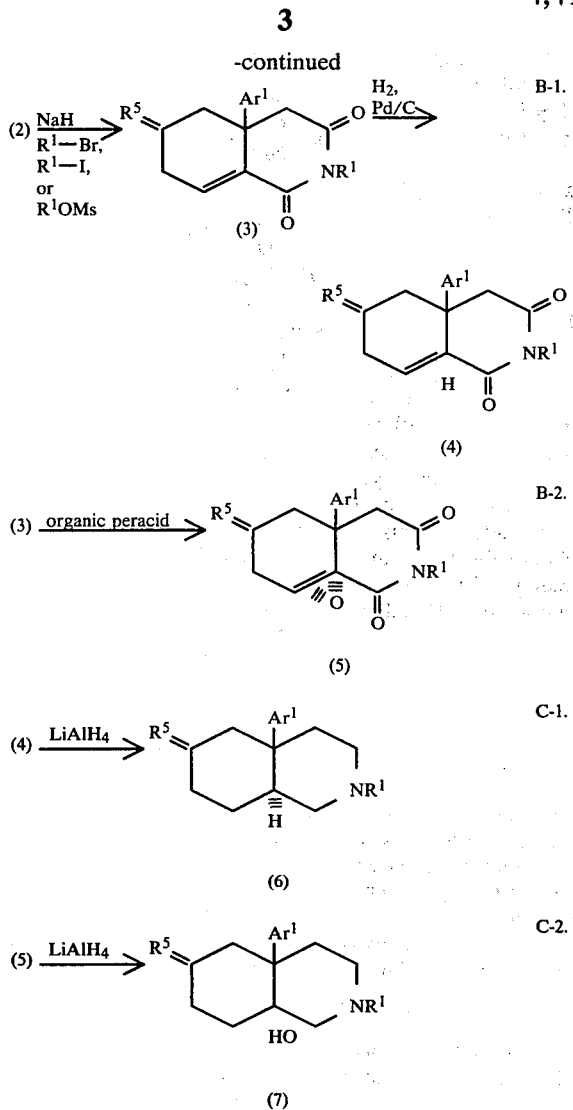

In the foregoing formulas (1) through (7), the groups $R^1$ have the values given previously. $R^5$ is

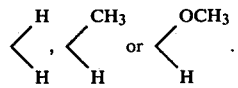

$R^6$ is $C_1$ to $C_4$ alkyl. $Ar^1$ is

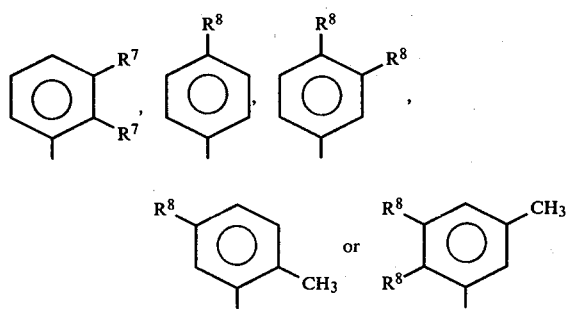

in which $R^7$ is hydrogen or methoxyl;

$R^8$ is methoxyl and jointly two of $R^7$ or of $R^8$ situated on adjacent carbons may be combined to form a divalent methylenedioxy group.

In Step A reactant $R^6OH$, which is also the reaction medium, is generally used in excess but to insure maximum yield should be used in the amount of at least one mole per mole of cyanoester. Likewise the HCl reactant may be used in excess but to insure maximum yield should be present in the amount of at least one mole per mole of cyanoester. The reaction is run in the liquid phase under anhydrous conditions. The reaction temperature should be in the range of about 50° to about 120° C. The reaction pressure is not critical, ordinarily being atmospheric for convenience but should be consistent with achievement of the stated reaction temperature.

In step B-1, the hydrocarbyl group of the hydrocarbyl bromide or iodide reactant corresponds to $R^1$ in the general formula I. Such hydrocarbyl bromides, iodides, or mesylates are readily available, as indicated in the following Table:

TABLE I

| $R^1$ | Source |
|---|---|
| $C_1$ to $C_6$ Alkyl | Commercially available |
| Cyclohexylmethyl | Commercially available |
| Benzyl | Commercially available |
| Phenethyl | Commercially available |
| Cyclopropylmethyl | Kirmse et al. Ber., 99, 2855 (1966) |
| Cyclobutylmethyl | Krug et al., J. Am. Chem. Soc., 76, 3222 (1954) |
| Cyclopentylmethyl | Smith et al., J. Org. Chem., 21, 1448 (1956). |

In the preparation of a 2-cyano-3-phenyl-3-carbalkoxymethylcyclohexene, the Boekelheide and Schilling procedure involves basically starting with cyclohexanone, as follows:

a. Cyclohexanone→2-chlorocyclohexanone (Horning, Organic Syntheses, Coll. Vol. III, 1955 p. 188)

b. 2-Chlorocyclohexanone→2-phenylcyclohexanone [Newman et al. J. Am. Chem. Soc. 66, 1551 1944). An alternative method is shown by T. Kametani et al., J. Chem. Soc. (C), 1047 (1971) in which a chloro-substituted benzene is reacted with cyclohexanone in the presence of sodium amide to produce a 2-arylcyclohexanone.]

c. 2-Phenylcyclohexanone→2-phenyl-2-carbethoxycyclohexanone [Newman et al., J. Am. Chem. Soc. 69, 942 (1947)].

d. 2-Phenyl-2-carbethoxycyclohexanone→2-cyano-3-phenyl-3-carbethoxycyclohexene.

These preliminary steps lead to various equivalents defined by the various values of Ar and $R^2$ in general formula I through starting with appropriately substituted cyclohexanones in step (a) and with appropriately substituted arylmagnesium bromides (or substituted chlorobenzenes in the alternative method) as intermediates in step (b). Thus, 4-methylcyclohexanone and 4-methoxycyclohexanone, which are commercially available, can be used as basic starting materials to produce compounds of formula I in which $R^2$ is

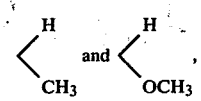

respectively.

The compounds of formula I in which $R_2$ ($R^5$ in the process description) is

serve as intermediates to compounds of Formula I in which $R^2$ has other values. The following Table II shows the additional $R^2$ values and the known methods by which they may be obtained.

TABLE II

| $R^2$ | Procedure |
|---|---|
| H, OH | Demethylation of the methoxy compound |
| H, OCCH$_3$ (‖O) | Acetylation of the hydroxy compound |
| =O | Oxidation of the hydroxy compound |
| CH$_3$, OH | Reaction of the oxo compound with methyllithium |
| CH$_3$, OCCH$_3$ (‖O) | Acetylation of the CH$_3$, OH compound |
| H, Cl | Reaction of the hydroxy compound with a strong chloridation agent, e.g., thionyl chloride |
| F, F | Reaction of the oxo compound with sulfur tetrafluoride [(Martin et al. J. Org. Chem. 27, 3164 (1962)]. |

Likewise, the use of appropriately substituted phenyl bromides in the preparation of the arylmagnesium bromide Grignard reactant (or substituted chlorobenzenes in the alternative method) for step (b) lead to corresponding Ar groups (Ar$^1$ in the process description) in the products of formula I. The following Table III shows pertinent Ar$^1$ groups with substituent $R^7$ and $R^8$ groups as defined above.

TABLE III

| Ar$^1$ | Source |
|---|---|
| phenyl with $R^7$, $R^{7a}$ | Bromides in which $R^7$ is hydrogen or methoxyl and $R^{7a}$ is hydrogen are commercially available. The bromide in which $R^7$ is hydrogen and $R^{7a}$ is methoxyl is also commercially available. The bromide in which both $R^7$ and $R^{7a}$ are methoxyl is obtainable by the method of Mason, J. Am. Chem. Soc. 69, 2241 (1947). |
| phenyl with $R^{8a}$, $R^8$ | The bromides in which $R^8$ and $R^{8a}$ are both methoxyl, and in which $R^8$ is hydrogen and $R^{8a}$ is methoxyl, are commercially available. The bromide in which $R^8$ and $R^{8a}$ are combined to form dioxymethylene is also commercially available. |
| phenyl with $R^8$, CH$_3$ | 3-Bromo-4-methylanisole is obtainable by the method of Mueller et al., Ann. 645, 92 (1961). |
| phenyl with $R^8$, CH$_3$, $R^8$ | 2-Bromo-4-methyl-6-methoxyphenol, serves via methylation to form 3-methyl-5,6-dimethoxyphenyl bromide [cf., Ueda et al., Chem. Abs. 58, 3419 (1963)] |

Compounds in which Ar$^1$ has methoxyl substituents (as in Table III) serve as intermediates to compounds of Formula I in which Ar has hydroxyl or acetoxyl substituents by using methods for conversion of $R^5$ groups to $R^2$ groups as shown in Table II.

SPECIFIC EMBODIMENTS OF THE INVENTION

In the following illustrative examples all parts are by weight and all temperatures are Centigrade unless otherwise stated.

EXAMPLE 1

N-Methyl-4a-phenyl-trans-decahydroisoquinoline

A. 2-Cyano-3-phenyl-3-carbethoxymethylcyclohexene

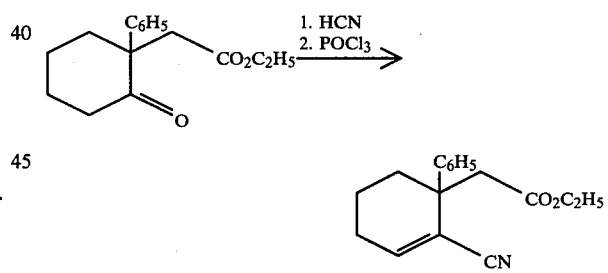

2-Carbethoxymethyl-2-phenylcyclohexanone (Boekelheide, et al., above) (90 g., 0.346 mole), 200 ml of hydrogen cyanide and 12 drops of a saturated aqueous solution of potassium cyanide was stirred at 0° C. overnight. Concentrated sulfuric acid (15 drops) was then added and the excess hydrogen cyanide evaporated. The crude cyanohydrin was taken up in ether and washed with cold 10% sulfuric acid solution, then dried with Na$_2$SO$_4$ and evaporated. The residual oil was dissolved in 500 ml of pyridine and 100 ml of phosphorus oxychloride was added. The reaction mixture was stirred under nitrogen at reflux for 5 hours then allowed to stand at 25° C. overnight. It was then carefully poured into a mixture of 2 liters of ice-water and 400 ml of concentrated hydrochloric acid and extracted with ether. The ether extract was washed with dilute hydrochloric acid, water and brine, then dried (Na$_2$SO$_4$) and evaporated. The residual oil was distilled, yielding 45 g of pale yellow liquid, bp 135° C. (0.20 mm), identified as 2-cyano-3-phenyl-3-carbethoxymethylcyclohexene.

NMR (CDCl₃)[(2)]: triplet at 64, 71, 78 cps, 3H (—OCH₂CH₃); methylene envelope from 70–150 cps, ca 6H; singlet at 178 cps, 2H

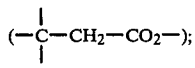

quartet at 234, 242, 249, 256, 2H (—OCH₂CH₃); triplet at 406, 419, 414, 1H

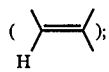

singlet at 436 cps, 5H (aromatic H).
[(2)] Peaks reported in cps from tetramethylsilane (TMS).

IR (neat): 4.50μ (C≡N); 5.5 and 5.85μ (lactone impurity); 5.75μ (—CO₂—).

B. 4a-Phenyl-1,3-diketo-1,2,3,4,4a,5,6,7-octahydroisoquinoline

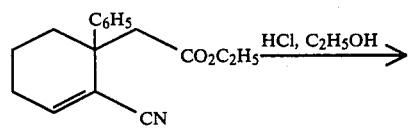

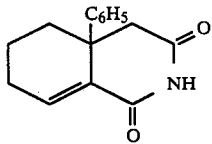

The product of Part A (50 g), dissolved in a minimum amount of absolute ethanol, was added to 2.5 liters of absolute ethanol previously saturated with anhydrous hydrogen chloride. The solution was refluxed under nitrogen for 48 hours. It was then cooled and concentrated to about 300 ml on a rotary evaporator. On cooling, a white crystalline solid precipitated which was filtered, washed with cold ethanol, and dried to yield 25 g (56%) of 4a-phenyl-1,3-diketo-1,2,3,4,4a,5,6,7-octahydroisoquinoline, mp 241°–3°.

Anal. Calcd for C₁₅H₁₅NO₂: C, 74.65; H, 6.26; N, 5.81. Found: C, 74.67; H, 6.25; N, 5.65.

C. N-Methyl-4a-phenyl-1,3-diketo-1,2,3,4,4a,5,6,7-octahydroisoquinoline

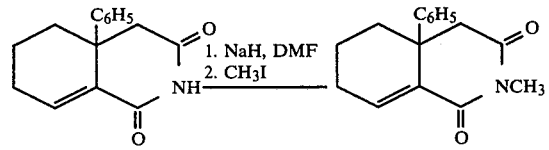

The product of Part B (7.20 g, 29.9 mmoles) in 50 ml of dry dimethylformamide was added to 1.58 g of a 55.5% suspension of sodium hydride in mineral oil (36.5 mmoles NaH), while the reaction mixture was maintained at 70° C. under nitrogen. When evolution of hydrogen ceased (about 1 hour) the reaction mixture was cooled to 25° C. and a solution of methyl iodide (8.52 g, 60 mmoles) in 20 ml of dimethylformamide was added dropwise. The mixture was then heated to 90°–100° C. for 2 hours, after which it was cooled, poured into ice-water and extracted with ether. The ether was evaporated and the residue recrystallized from ethanol to yield 6.56 g (86%) of N-methyl-4a-phenyl-1,3-diketo-1,2,3,4,4a,5,6,7-octahydroisoquinoline.

Anal. Calcd. for C₁₆H₁₇O₂N: C, 75.27; H, 6.71; N, 5.49. Found: C, 75.22; H, 6.71; N, 5.71.

Using an analogous procedure but substituting cyclohexylmethyl bromide for methyl iodide, N-cyclohexylmethyl-4a-phenyl-1,3-diketo-1,2,3,4,4a,5,6,7-octahydroisoquinoline was prepared. Similarly, substituting cyclopropylmethyl bromide or mesylate and cyclobutylmethyl bromide for methyl iodide, N-cyclopropylmethyl-4a-phenyl-1,3-diketo-1,2,3,4,4a,5,6,7-octahydroisoquinoline and N-cyclobutylmethyl-4a-phenyl-1,3-diketo-1,2,3,4,4a,5,6,7-octahydroisoquinoline, respectively, were prepared.

D. N-Methyl-4a-phenyl-1,3-diketo-trans-decahydroisoquinoline

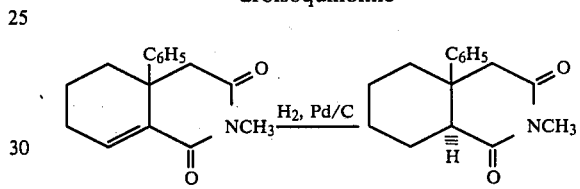

A mixture of the product of Part C (2.0 g, 7.85 mmoles), 175 ml of absolute ethanol, and 300 mg of 5% palladium on carbon was shaken under 40 psi of hydrogen for 24 hours. The catalyst was removed by filtration and the solvent evaporated from the filtrate. Recrystallization of the residue from ethanol gave 1.8 g (90%) of N-methyl-4a-phenyl-1,3-diketo-trans-decahydroisoquinoline, mp 151°–153° C.

Anal. Calcd. for C₁₆H₁₈NO₂: C, 74.66; H, 7.44; N, 5.44. Found: C, 74.74; H, 7.66; N, 5.33.

In an analogous procedure reduction of the N-hydrocarbyl-4a-phenyl-1,3-diketo-1,2,3,4,4a,5,6,7-octahydroisoquinolines described in Part C, yielded N-cyclohexylmethyl-4a-phenyl-1,3-diketo-trans-decahydroisoquinoline, N-cyclopropylmethyl-4a-phenyl-1,3-diketo-trans-decahydroisoquinoline and N-cyclobutylmethyl-4a-phenyl-1,3-diketo-trans-decahydroisoquinoline, respectively.

E. N-Methyl-4a-phenyl-trans-decahydroisoquinoline

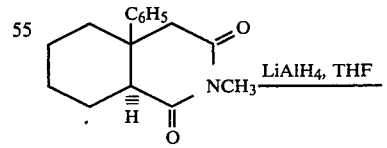

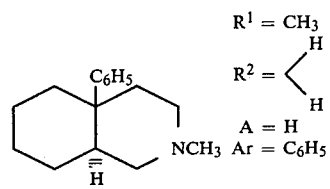

$R^1 = CH_3$
$R^2 = \begin{cases} H \\ H \end{cases}$
$A = H$
$Ar = C_6H_5$

The product of Part D (1.34 g, 5.2 mmoles) in 40 ml of sodium-dried tetrahydrofuran was treated under nitrogen, with 1.34 g of lithium aluminum hydride. The mixture was refluxed for 24 hours, then cooled and quenched by successive additions of 1.3 ml of water, 1.3 ml of 15% aqueous sodium hydroxide and 3.9 ml of water. The inorganic salts were filtered and washed with ether, and the combined filtrates were dried ($K_2CO_3$) and evaporated to a clear oil. This residual oil was taken up in 10 ml of absolute ethanol and treated with 30 ml of a saturated solution of picric acid in ethanol. The resulting precipitate was filtered and dried, then recrystallized from ethanol, yielding 1.80 g of picrate, mp 217.5–219.5 (corr.).

Anal. Calcd. for $C_{22}H_{26}N_4O_7$: C, 57.63; H, 5.72; N, 12.42. Found: C, 57.49; H, 5.55; N, 11.91.

The picrate was chromatographed on a 1"×6" column of neutral Woelm alumina I (packed in methylene chloride) and eluted first with methylene chloride then with 5% ethanol-methylene chloride, the eluates being 440 mg of a clear oil followed by 390 mg of yellow-green material. The latter portion was taken up in methylene chloride and washed with aqueous ammonium hydroxide, then dried ($K_2CO_3$) and concentrated. The residual oil was evaporatively distilled, bp 100° C. (0.07 mm), to give 300 mg of an oil which was combined with the 440 mg portion to yield 740 mg (62% from imide). This oil solidified on standing to give white crystalline N-methyl-4a-phenyl-trans-decahydroisoquinoline, mp 72°–73° C.

Anal. Calcd. for $C_{16}H_{23}N$: C, 83.77; H, 10.10; N, 6.11. Found: C, 83.76; H, 10.23; N, 5.84.

Similarly, lithium aluminum hydride reduction of the N-hydrocarbyl-4a-phenyl-1,3-diketo-trans-decahydroisoquinolines of Part D gave N-cyclohexylmethyl-4a-phenyl-trans-decahydroisoquinoline, N-cyclopropylmethyl-4a-phenyl-trans-decahydroisoquinoline, and N-cyclobutylmethyl-4a-phenyl-trans-decahydroisoquinoline, respectively.

EXAMPLE 2 laevo- and dextro-N-Methyl-4a-phenyl-trans-decahydroisoquinoline

A. laevo- and dextro-2-Carboxymethyl-2-phenylcyclohexanone α-phenethylamine salt

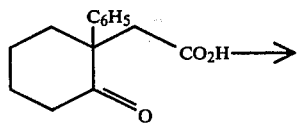

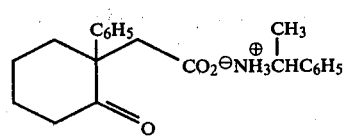

1. 2-Carboxymethyl-2-phenylcyclohexanone (Boekelheide et al., above) (40 g, 0.154 mole) obtained by alkaline hydrolysis of 2-carbethoxymethyl-2-phenylcyclohexanone was dissolved in 140 ml of hot ethanol and treated with 27 g of (+)-α-phenethylamine. The mixture was allowed to slowly crystallize to yield 21.8 g of the l-salt, m.p. 130°–132°, $[\alpha]_D$ −94. A second recrystallization from ethanol yielded material with m.p. 137°–139°, $[\alpha]_D^{25°}$ −142°. Further recrystallizations did not change the optical rotation.

2. The mother liquors from above were taken up in 6 N hydrochloric acid and the free acid extracted with ether. This material was dissolved in ethanol, treated with (−)-α-phenethylamine, and allowed to slowly crystallize. The white crystalline d-salt had m.p. 136°–137.5°, $[\alpha]_D^{25°}$ +141°.

B. laevo- and dextro-2-Carboxymethyl-2-phenylcyclohexanone

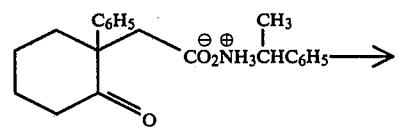

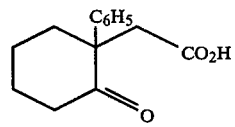

1. A solution of the product of Part A-1 (14.0 g) in 250 ml of cold 6 N hydrochloric acid was extracted with ether. The ether extracts were dried with anhydrous magnesium sulfate, filtered, and the ether evaporated to yield 9.6 g of the l-ketoacid m.p. 94°–95° $[\alpha]_D^{25°}$ −194 (c 1.04, $CHCl_3$).

2. A solution of the product of Part A-2 (15.9 g) in 250 ml of cold 6 N hydrochloric acid was extracted with ether and treated as above to yield 10.0 g of the d-ketoacid m.p. 94°–95°, $[\alpha]_D^{25°}$ +193° (1.03, $CHCl_3$).

C. laevo- and dextro-2-Carbethoxymethyl-2-phenylcyclohexanone

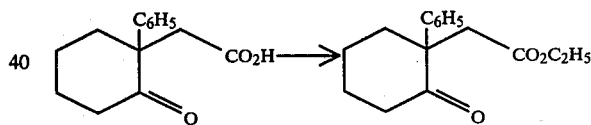

1. A solution of the product of Part B-1 (28 g) in 700 ml of ethanol containing 3 ml of concentrated sulfuric acid was refluxed in a soxhlet extractor apparatus with the thimble filled with 3A molecular sieves. After refluxing for 24 hrs, excess potassium carbonate was added. The mixture was filtered and the solution evaporated. The residue was distilled to yield l-ketoester, a clear oil, b.p. 125° (0.1 mm), $[\alpha]_D^{25°}$ −207° (c 1.5, $CHCl_3$).

2. A solution of the product of Part B-2 (40 g) in 1000 ml of ethanol containing 8 ml of concentrated sulfuric acid was treated as above to yield, after distillation, the d-ketoester as a clear oil, b.p. 125° (0.1 mm), $[\alpha]_D^{25°}$ +234° (c 1.00, $CHCl_3$).

D. laevo- and dextro-2-Cyano-3-phenyl-3-carbethoxymethylcyclohexene

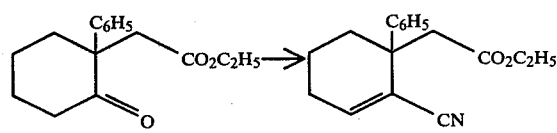

1. The product of Part C-1 (36 g, 0.138 mole), 200 ml of hydrogen cyanide and 12 drops of a saturated aqueous solution of potassium cyanide was stirred at 0° overnight. Concentrated sulfuric acid was added and the excess hydrogen cyanide evaporated. The residue was taken up in either, washed successively with 0.1 N sulfuric acid, and brine, dried (Na2SO4), and evaporated. The residual oil was dissolved in 250 ml of pyridine and 50 ml of phosphorous oxychloride was added. The reaction mixture was stirred, under nitrogen, at reflux for 5 hours, then allowed to stand at 25° overnight. It was then poured into a mixture of 1 liter of ice-water and 200 ml of concentrated hydrochloric acid, and the resulting mixture was extracted with ether. The ether extract was washed with dilute hydrochloric acid, water and brine, then dried (Na2SO4) and evaporated. The residual oil was distilled yielding 28 g of the 1-cyanoester, b.p. 130° (0.1 mm).

2. The product of Part C-2 (35 g, 0.134 mole) was treated as above to obtain 25 g of the d-cyanoester, b.p. 130° (0.1 mm).

E. dextro- and laevo-4a-Phenyl-1,3-diketo-1,2,3,4a,5,6,7-octahydroisoquinoline

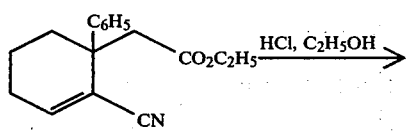

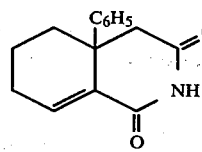

1. The product of Part D-1 (28 g), dissolved in 50 ml of absolute ethanol, was added to 600 ml of absolute ethanol previously saturated with anhydrous hydrogen chloride. The solution was refluxed under nitrogen for 48 hours. It was then cooled and concentrated. A white crystalline solid precipitated which was filtered, then recrystallized from ethanol to yield 12.0 g of the unsaturated d-imide, $[\alpha]_D^{25°} +219$ (c 1.00, CHCl3).

2. The product of Part D-2 (17 g) in 40 ml of absolute ethanol was added to 400 ml of absolute ethanol previously saturated with anhydrous hydrogen chloride, then treated as above to yield 8.9 g of the unsaturated 1-imide, m.p. 169°–170°, $[\alpha]_D^{25°} -208$ (c 1.20, CHCl3).

In this example the sign of rotation changes in the ring-closing reactions.

F. dextro- and laevo-N-Methyl-4a-phenyl-1,3-diketo-1,2,3,4,4a,5,6,7-octahydroisoquinoline

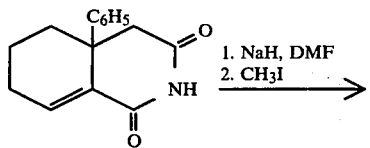

-continued

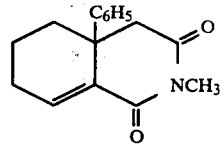

1. The product of Part E-1 (7.2 g, 29.9 mmoles) in 50 ml of dry dimethylformamide was added to 1.58 g of a 55.5% suspension of sodium hydride in mineral oil (36.5 mmoles NaH) in 50 ml dimethylformamide, while the reaction mixture was maintained at 70° under nitrogen. The mixture was stirred and heated at 70° for 1 hour after the addition was completed, then cooled, and methyl iodide (8.5 g) in 20 ml of dimethylformamide was added dropwise. The mixture was heated at 90° for 30 min. then allowed to stand overnight at 25°. It was poured into water and extracted with ether. The ether extracts were dried (Na2SO4) and evaporated and the residue recrystallized from ethanol to yield 6.17 g of the unsaturated d-N-methylimide, m.p. 156°–158°, $[\alpha]_D^{25°} +245°$ (c 1.25, CHCl3).

2. The product of Part E-2 (8.94 g, 37.1 mmole) in 60 ml of dimethylformamide was added to 1.96 g of a 55.5% suspension of sodium hydride in mineral oil in 50 ml of dimethylformamide as above to yield, after recrystallization in ethanol, 6.0 g of the unsaturated 1-N-methylimide, m.p. 149°–153°, $[\alpha]_D^{25°} -258°$.

G. dextro- and laevo-N-Methyl-4a-phenyl-1,3-diketo-trans-decahydroisoquinoline

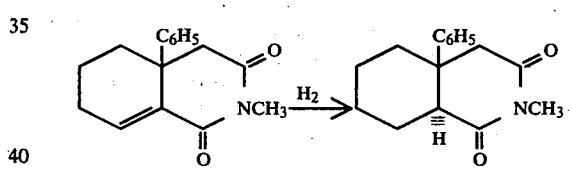

1. A mixture of the product of Part F-1 (6.1 g, 23.9 mmole), 100 ml of glacial acetic acid and 2 g of 5% palladium on carbon was shaken under 40 psi of hydrogen for 24 hours. The catalyst was removed by filtration and the solvent evaporated. Recrystallization of the residue from ethanol gave 3.7 g of the trans saturated d-N-methylimide, m.p. 189°–181°, $[\alpha]_D^{25°} +81°$.

2. The product of Part F-2 (6.0 g, 23.5 mmoles) was treated as above to obtain 4.0 g of the trans saturated 1-N-methylimide, m.p. 159°–160°, $[\alpha]_D^{25°} -72°$ (c, 1.02, CHCl3).

H. laevo- and dextro-N-Methyl-4a-phenyl-trans-decahydroisoquinoline

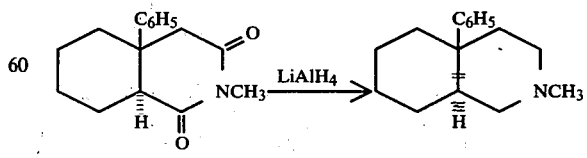

1. The product of Part G-1 (3.5 g, 13.6 mmole) in 50 ml of sodium-dried tetrahydrofuran was treated under nitrogen with 4.0 g of lithium aluminum hydride. The mixture was refluxed for 24 hours, then cooled and quenched by successive additions of 4.0 ml of water, 4.0 ml of 15% aqueous sodium hydroxide and 12.0 ml of water. The inorganic salts were filtered and washed with ether, and the combined filtrates were dried ($K_2CO_3$) and evaporated to yield 2.75 g of a clear oil. Purification via the picrate (m.p. 186.5°–188°) yielded white crystalline 1-N-methyl-4α-phenyl-trans-decahydroisoquinoline, m.p. 67.2°–67.6°, $[\alpha]_D^{25°}+2°$ (c 1.10, $CHCl_3$), $[\alpha]_{436}^{25°}-3°$, $[\alpha]_{405}^{25°}-8°$, and $[\alpha]_{365}^{25°}-21°$.

2. The product of Part G-2 (3.43 g, 13.3 mmole) was treated as above to obtain 2.6 g of d-N-methyl-4α-phenyl-trans-decahydroisoquinoline, m.p. 66.5°–67°, $[\alpha]_D^{25°}$ 0°, $[\alpha]_{436}^{25°}+1.3$, $[\alpha]_{405}^{25°}+6.3$, $[\alpha]_{365}^{25°}+17.5$.

Note that in this example the sign of rotation again changes after the reduction with lithium aluminum hydride.

EXAMPLE 3

N-Methyl-4a-(m-methoxyphenyl)-trans-decahydroisoquinoline

A.

2-Cyano-3-carbethoxymethyl-3-(m-methoxyphenyl)-cyclohexene

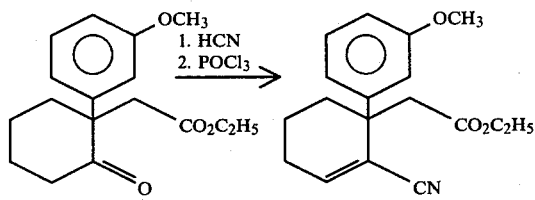

A mixture of 2-carbethoxymethyl-2-(m-methoxyphenyl)cyclohexanone, Langlois et al., Tetrahedron 27, 5641 (1971), (25 g, 86.3 mmoles), 100 ml of hydrogen cyanide and 4 drops of a saturated aqueous potassium cyanide solution was stirred at 0° C. under nitrogen, for 24 hours. After this time, 5 drops of concentrated sulfuric acid was added and the excess hydrogen cyanide evaporated. The residual oil was taken up in ether and washed with 10% aqueous sulfuric acid and then with brine, dried ($M_gSO_4$), and the ether evaporated. The crude cyanohydrin thus obtained was taken up in 175 ml of pyridine, 35 ml of phosphorus oxychloride was added, and the solution was stirred at reflux, under nitrogen, for 3 hours. It was then cooled and poured into a mixture of 500 ml of ice-water and 100 ml of concentrated hydrochloric acid, and the resulting mixture was extracted with ether. After washing the ether extract with brine, drying and concentrating, 22 g of crude product was obtained. This was distilled by short path distillation to yield 16 g, bp 166° C. (0.5 mm). The infrared spectrum of this material indicated it to be 2-cyano-3-carbethoxymethyl-3-(m-methoxyphenyl)cyclohexene with a small amount of an impurity, probably a lactone, with bands at 5.50μ and 5.85μ. The material was considered of sufficient purity to carry it on to the next step.

Anal. Calcd. for $C_{18}H_{21}O_3N$: C, 72.20; H, 7.07; N, 4.68. Found: C, 72.22, H, 7.13; N, 4.10.

B.

4a-(m-Methoxyphenyl)-1,3-diketo-1,2,3,4,4a,5,6,7-octahydroisoquinoline

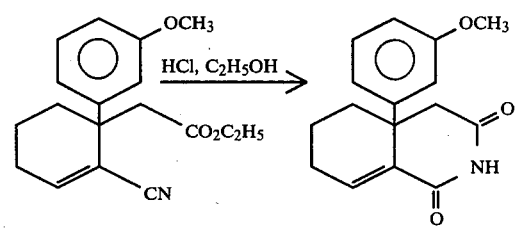

The product of Part A (16 g, 53.5 mmoles) dissolved in absolute ethanol was added to 1.5 liters of absolute ethanol previously saturated with anhydrous hydrogen chloride. The solution was refluxed, under nitrogen, for 48 hours and then allowed to stand at 25° C. for 24 hours. It was concentrated on a rotary evaporator to about 500 ml, cooled in ice, and the resulting crystalline precipitate filtered to yield 8.0 g (55%) of 4a-(m-methoxyphenyl)-1,3-diketo-1,2,3,4,4a,5,6,7-octahydroisoquinoline, mp 230°–232°.

Anal. Calcd. for $C_{16}H_{17}NO_3$: C, 70.83; H, 6.31; N, 5.16. Found: C, 70.97; H, 6.33; N, 5.59.

In an analogous procedure, various 1,3-diketo compounds are prepared from corresponding 3-carbethoxymethyl-2-cyanocyclohexenes as indicated in the following table which shows the substituent Ar and $R^2$ groups in each pair.

TABLE IV

| Pair | Ar | $R^2$ |
|---|---|---|
| 1 | 3-Methoxyphenyl | H, OCH$_3$ |
| 2 | 2-Methoxyphenyl | H, H |
| 3 | 2-Methoxyphenyl | H, OCH$_3$ |
| 4 | 4-Methoxyphenyl | H, H |
| 5 | 4-Methoxyphenyl | H, OCH$_3$ |
| 6 | 2,3-Dimethoxyphenyl | H, H |
| 7 | 2,3-Dimethoxyphenyl | H, OCH$_3$ |
| 8 | 3,4-Dimethoxyphenyl | H, H |

TABLE IV-continued

| Pair | Ar | R² | |
|---|---|---|---|
| 9 | 3,4-Dimethoxyphenyl | H | OCH₃ |
| 10 | 3,4-(Methylenedioxy)phenyl | H | H |
| 11 | 3,4-(Methylenedioxy)phenyl | H | OCH₃ |
| 12 | 2-Methyl-5-methoxyphenyl | H | H |
| 13 | 2-Methyl-5-methoxyphenyl | H | OCH₃ |
| 14 | 2,3-Dimethoxy-5-methylphenyl | H | H |
| 15 | 2,3-Dimethoxy-5-methylphenyl | H | OCH₃ |
| 16 | Phenyl | H | CH₃ |
| 17 | 3-Methoxyphenyl | H | CH₃ |
| 18 | 2-Methoxyphenyl | H | CH₃ |
| 19 | 4-Methoxyphenyl | H | CH₃ |
| 20 | 2,3-Dimethoxyphenyl | H | CH₃ |
| 21 | 3,4-Dimethoxyphenyl | H | CH₃ |
| 22 | 3,4-(Methylenedioxy)phenyl | H | CH₃ |
| 23 | 2-Methyl-5-methoxyphenyl | H | CH₃ |
| 24 | 2,3-Dimethoxy-5-methylphenyl | H | CH₃ |

C. N-Methyl-4a-(m-methoxyphenyl)-1,3-diketo-1,2,3,4,4a,5,6,7-octahydroisoquinoline

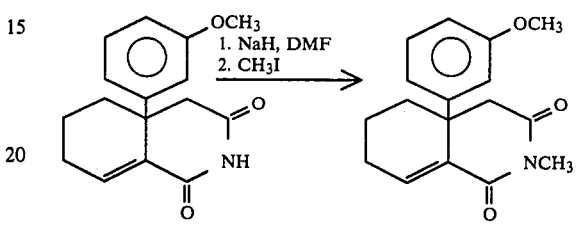

The product of Part B (4.07 g, 15 mmoles) in 50 ml of dry dimethylformamide was added to a mixture of 790 mg of a 55% suspension of sodium hydride (18.1 mmoles of NaH) in mineral oil in 25 ml of dimethylformamide while the temperature of the reaction mixture was maintained at 60°–70° C. under nitrogen. After the addition was complete, the reaction mixture was heated at 90° C. for 2 hours, by which time evolution of hydrogen had ceased. It was then cooled to 30° C. whereupon a solution of 4.25 g (30 mmoles) of methyl iodide in 10 ml of dimethylformamide was added dropwise. The mixture was heated at 90°–100° C. for 2 hours, then cooled, poured into ice-water and extracted with ether. The ether extracts were washed with water, dried (MgSO₄) and evaporated. The residue was recrystallized from ethanol to yield crystalline N-methyl-4a-(m-methoxyphenyl)-1,3-diketo-1,2,3,4,4a,5,6,7-octahydroisoquinoline (3.8 g, 89%), mp 139°–141°.

Anal. Calcd. for $C_{17}H_{19}NO_3$: C, 71.54; H, 6.71; N, 4.91. Found: C, 71.58; H, 6.93; N, 4.94.

By substitution in this procedure of the methyl iodide by any of the following: phenethyl bromide, cyclohexylmethyl bromide, cyclopropylmethyl bromide, cyclobutylmethyl bromide, the corresponding N-phenethyl-, N-cyclohexylmethyl-, N-cyclopropylmethyl-, or N-cyclobutylmethyl-, 4a-(m-methoxyphenyl)-1,3-diketo-1,2,3,4,4a,5,6,7-octahydroisoquinolines are obtained. Similarly, substitution of the 4a-(m-methoxyphenyl)-1,3-diketo-1,2,3,4,4-a,5,6,7-octahydroisoquinoline by any of the 4a-aryl-1,3-diketo-1,2,3,4,4a,5,6,7-octahydroisoquinolines, 4a-aryl-6-methoxy-1,3-diketo-1,2,3,4,4a,5,6,7-octahydroisoquinolines, or 4a-aryl-6-methyl-1,3-diketo-1,2,3,4,4a,5,6,7-octahydroisoquinolines described in Part B yields the corresponding N-hydrocarbyl-4a-aryl-1,3-diketo-1,2,3,4,4a,5,6,7-octahydroisoquinolines, N-hydrocarbyl-4a-aryl-6-methoxy-1,3-diketo-1,2,3,4,4a,5,6,7-octahydroisoquinolines, or N-hydrocarbyl-4a-aryl-6-methyl-1,3-diketo-1,2,3,4,4a,5,6,7-octahydroisoquinolines.

D.
N-Methyl-4a-(m-methoxyphenyl)-1,3-diketo-trans-decahydroisoquinoline

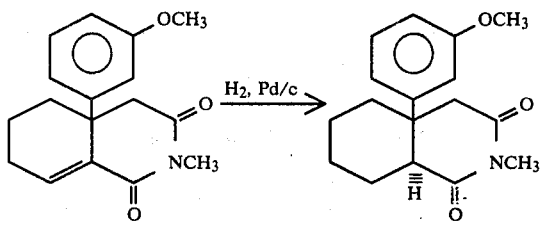

The product of Part C (3.2 g, 11.21 mmoles), 100 ml of glacial acetic acid, 50 ml of dioxane and 700 mg of 5% palladium-on-carbon were shaken under 40 psi of hydrogen for 24 hours. The catalyst was then filtered off and washed well with dioxane, and the combined filtrate was concentrated to a clear oil, yield 3.2 g (99.4%). The product was pure N-methyl-4a(m-methoxyphenyl)-1,3-diketo-trans-decahydroisoquinoline, as determined by thin-layer chromatography (20% ether-benzene on silica gel plates) and by its nmr spectrum.

NMR (CDCl$_3$): complex multiplet at 50–150 cps from TMS (9H, —CH$_2$— and

quartet at 148, 163, 173, 189 cps (2H, —CH$_2$—CO—); singlet at 180 cps (3H, NCH$_3$); singlet at 200 cps (3H, OCH$_3$); multiplet at 397–420 cps (4H, Ar—H).

In the same manner, catalytic reduction of the analogous products from Part C gives the corresponding N-hydrocarbyl-4a-aryl-1,3-diketo-trans-decahydroisoquinolines, N-hydrocarbyl-4a-aryl-6-methoxy-1,3-diketo-trans-decahydroisoquinolines, and N-hydrocarbyl-4a-aryl-6-methyl-1,3-diketo-trans-decahydroisoquinolines.

E.
N-Methyl-4a-(m-methoxyphenyl)-trans-decahydroisoquinoline

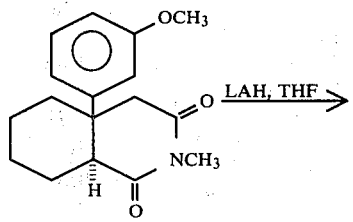

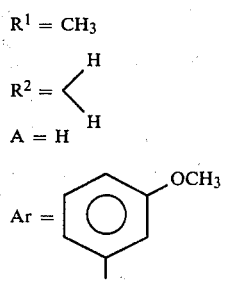

The product of Part D (3.2 g, 11.2 mmoles) in 75 ml of sodium-dried tetrahydrofuran was treated with 3.2 g (84.2 mmoles) of lithium aluminum hydride. The reaction mixture was kept under nitrogen and refluxed for 20 hours. It was then allowed to cool to 25° C. and treated successively with 3.2 ml of water, 3.2 ml of 15% aqueous sodium hydroxide and 9.6 ml of water. The precipitated inorganic salts were filtered and washed well with ether. The combined filtrates were dried over anhydrous potassium carbonate and evaporated to an oil. This oil was evaporatively distilled to yield, 2.0 g (69%) of N-methyl-4a-(m-methoxyphenyl)-trans-decahydroisoquinoline as a clear oil, bp 116° C. (0.07 mm).

Anal. Calcd for C$_{17}$H$_{25}$NO: C, 78.71; H, 9.71; N, 5.40. Found: C, 78.14; H, 9.05; N, 5.08.

In a similar fashion, lithium aluminum hydride reduction of the analogous products of Part D gives the corresponding N-hydrocarbyl-4a-aryl-trans-decahydroisoquinolines, N-hydrocarbyl-4a-aryl-6-methoxy-trans-decahydroisoquinolines, N-hydrocarbyl-4a-aryl-6-methyl-trans-decahydroisoquinolines.

EXAMPLE 4
N-Methyl-4-m-hydroxyphenyl)-trans-decahydroisoquinoline

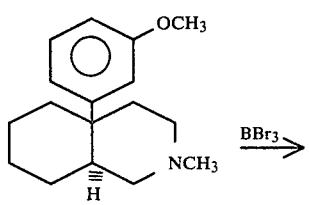

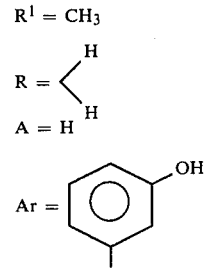

A solution of 800 mg of N-methyl-4a-(m-methoxyphenyl)-trans-decahydroisoquinoline (3.09 mmoles) in 30 ml of methylene chloride was added in portions to an ice-cold solution of 0.59 ml (1.55 g, 6.18 mmoles) of boron tribromide in 15 ml of methylene chloride. The solution, protected under nitrogen, was kept overnight at 25° C. Methanol (5 ml) was then added and the solution evaporated. The residue was treated with 15 ml of 5 N aqueous sodium hydroxide and the mixture stirred for 15 minutes. Ether (50 ml) was added and the bilayer mixture stirred for 2 hours. The aqueous and ether layers were finally separated and the aqueous portion saturated with carbon dioxide. The resulting solid precipitate was extracted with ether and the extract concentrated to give 680 mg of N-methyl-4a-(m-hydroxyphenyl)-trans-decahydroisoquinoline, mp 195°–205° C.

NMR (CDCl$_3$): methylene envelope from 60–160 cps from TMS; singlet at 127 cps (3H, NCH$_3$); multiplet at 127 cps (3H, NCH$_3$); multiplet at 383–432 cps (4H, Ar—H).

Anal. Calcd. for C$_{16}$H$_{23}$NO: C, 78.30; H, 9.44; N, 5.71. Found: C, 78.05; H, 9.47; N, 5.65.

In a similar manner, analogous methoxy-substituted products obtained as in Example 3, Part E, can be demethylated to corresponding hydroxy-substituted products. The following table shows Ar and R$^2$ substituents of such pairs.

TABLE

| Pair | Methoxy Compound Ar | R$^2$ | Hydroxy Compound Ar | R$^2$ |
|---|---|---|---|---|
| 1 | 2-Methoxyphenyl | H, H | 2-Hydroxyphenyl | H, H |
| 2 | 2-Methoxyphenyl | H, OCH$_3$ | 2-Hydroxyphenyl | H, OH |
| 3 | 4-Methoxyphenyl | H, H | 4-Hydroxyphenyl | H, H |
| 4 | 4-Methoxyphenyl | H, OCH$_3$ | 4-Hydroxyphenyl | H, OH |
| 5 | 2,3-Dimethoxyphenyl | H, H | 2,3-Dihydroxyphenyl | H, H |
| 6 | 2,3-Dimethoxyphenyl | H, OCH$_3$ | 2,3-Dihydroxyphenyl | H, OH |
| 7 | 3,4-Dimethoxyphenyl | H, H | 3,4-Dihydroxyphenyl | H, H |
| 8 | 3,4-Dimethoxyphenyl | H, OCH$_3$ | 3,4-Dihydroxyphenyl | H, OH |
| 9 | 2-Methyl-5-methoxyphenyl | H, H | 2-Methyl-5-hydroxyphenyl | H, H |
| 10 | 2-Methyl-5-methoxyphenyl | H, OCH$_3$ | 2-Methyl-5-hydroxyphenyl | H, OH |
| 11 | 2,3-Dimethoxy-5-methylphenyl | H, H | 2,3-Dihydroxy-5-methylphenyl | H, H |
| 12 | 2,3-Dimethoxy-5-methylphenyl | H, OCH$_3$ | 2,3-Dihydroxy-5-methylphenyl | H, OH |
| 13 | 3-Methoxyphenyl | H, CH$_3$ | 3-Hydroxyphenyl | H, CH$_3$ |
| 14 | 2-Methoxyphenyl | H, CH$_3$ | 2-Hydroxyphenyl | H, CH$_3$ |
| 15 | 4-Methoxyphenyl | H, CH$_3$ | 4-Hydroxyphenyl | H, CH$_3$ |
| 16 | 2,3-Dimethoxyphenyl | H, CH$_3$ | 2,3-Dihydroxyphenyl | H, CH$_3$ |
| 17 | 3,4-Dimethoxyphenyl | H, CH$_3$ | 3,4-Dihydroxyphenyl | H, CH$_3$ |
| 18 | 2-Methyl-5-methoxyphenyl | H, CH$_3$ | 2-Methyl-5-hydroxyphenyl | H, CH$_3$ |
| 19 | 2,3-Dimethoxy-5-methylphenyl | H, CH$_3$ | 2,3-Dihydroxy-5-methylphenyl | H, CH$_3$ |

EXAMPLE 5

N-Methyl-4a-phenyl-8a-hydroxy-trans-decahydroisoquinoline

A.

N-Methyl-4a-phenyl-1,3-diketo-8,8a-epoxydecahydroisoquinoline

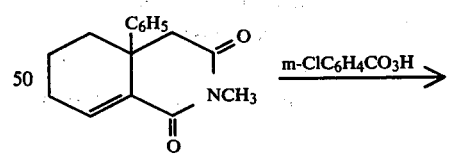

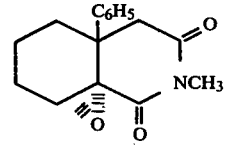

A solution of 1.0 g (3.92 mmoles) of N-methyl-4a-phenyl-1,3-diketo-1,2,3,4,4a,5,6,7-octahydroisoquinoline in 10 ml of chloroform was treated with a solution of 746 mg of 85% m-chloroperbenzoic acid in 12 ml of chloroform. The reaction mixture was refluxed for 36 hours, after which it was poured into 5 N sodium hydroxide. The aqueous phase was extracted twice with chloroform and the combined organic layers were washed well with water, then brine. Drying with sodium sulfate and evaporation of the solvent gave 0.7 g of white solid N-methyl-4a-phenyl-1,3-diketo-8,8a-epoxy-decahydroisoquinoline, mp 135°–140° C.

In the above example chloroperbenzoic acid has been used but it should be understood that any organic peracid can be used, as for example, perbenzoic, performic, peracetic, trifluoroperacetic, and the like.

In a similar way, analogous products from Example 3, Part C, are converted with m-chloroperbenzoic acid to the corresponding N-hydrocarbyl-4a-aryl-1,3-diketo-8,8a-epoxy-decahydroisoquinoline, N-hydrocarbyl-4a-aryl-1,3-diketo-6-methoxy-8,8a-epoxy-decahydroisoquinoline and N-hydrocarbyl-4a-aryl-1,3-diketo-6-methyl-8,8a-epoxy-decahydroisoquinoline.

B.
N-Methyl-4a-phenyl-8a-hydroxy-trans-decahydroisoquinoline

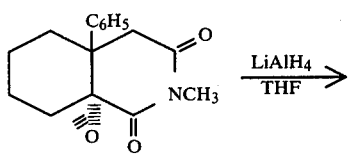

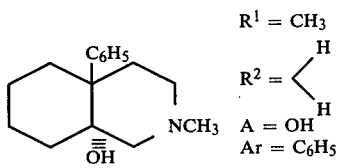

A mixture of 0.6 g of N-methyl-4a-phenyl-1,3-diketo-8,8a-epoxydecahydroisoquinoline and 1.0 g of lithium aluminum hydride in 25 ml of tetrahydrofuran was refluxed overnight. The reaction mixture was cooled, then 1 ml of water, 1 ml of 15% aqueous sodium hydroxide and finally 3 ml of water were added in succession. The mixture was diluted with 25 ml of ether and filtered to remove inorganic salts. The filtrate was concentrated by evaporation of solvents, the residue was taken up in ether, and the ether solution was dried ($K_2CO_3$). Evaporation of the dried solution and trituration of the residue with ethanol gave a white crystalline compound, mp 84°–87°, identified as N-methyl-4a-phenyl-8a-hydroxy-trans-decahydroisoquinoline.

NMR ($CDCl_3$): methylene envelope over 55–160 cps from TMS (12H, —$CH_2$—); singlet at 132 cps (3H, $NCH_3$); AB quartet at 140, 150, 171, 182 cps (2H, —C—$CH_2$—N—); broad singlet at 261 cps (1H, OH); complex multiplet at 427–459 cps (5H, ArH).

Anal. Calcd. for $C_{16}H_{23}NO$: C, 78.30; H, 9.44; N, 5.71. Found: C, 78.27; H, 9.57; N, 5.48.

In a similar way, analogous products from Part A above are treated with lithium aluminum hydride to yield the corresponding N-hydrocarbyl-4a-aryl-8a-hydroxy-trans-decahydroisoquinoline, N-hydrocarbyl-4a-aryl-6-methoxy-8a-hydroxy-trans-decahydroisoquinoline, and N-hydrocarbyl-4a-aryl-6-methyl-8a-hydroxy-trans-decahydroisoquinoline.

EXAMPLE 6
N-Cyclohexylmethyl-4a-phenyl-trans-decahydroisoquinoline

A.
N-Cyclohexylmethyl-4a-phenyl-1,3-diketo-1,2,3,4,4a,5,6,7-octahydroisoquinoline

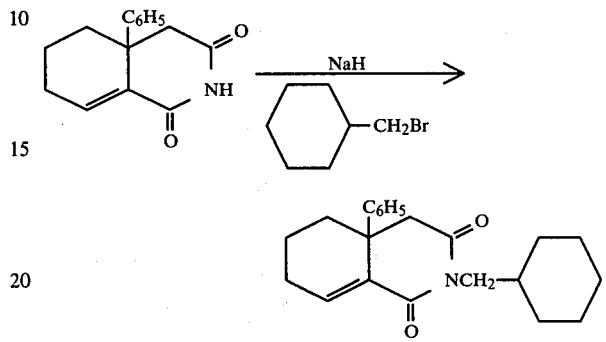

A solution of 4-a(phenyl)-1,3-diketo-1,2,3,4,4a,5,6,7-octahydroisoquinoline (2.0 g, 8.30 mmoles) in 15 ml of dry dimethylformamide was added dropwise to 395 mg of a 55% suspension of sodium hydride in mineral oil in 15 ml of dimethylformamide at 70°. The reaction mixture was heated for 1 hour at 70° C., then cooled to 25° C. Cyclohexylmethyl bromide (1.62 g) in 15 ml of dimethylformamide was added dropwise and the mixture was stirred overnight at 25°. After refluxing for 1 hour it was poured into water and extracted with ether. The resulting crude product was triturated with ethanol to yield 650 mg of solid. The mother liquors were then chromatographed on 100 g of Florisil and eluted with 4% acetone-hexane mixtures to yield an additional 825 mg, mp 111°–113°. The product was identified as N-cyclohexlmethyl-4a-phenyl-1,3-diketo-1,2,3,4,4a,5,6,7-octahydroisoquinoline.

Anal. Calcd for $C_{22}H_{27}NO_2$: C, 78.28; H, 8.06; N, 4.15. Found: C, 78.03; H, 7.80; N, 4.10.

B.
N-Cyclohexylmethyl-4a-phenyl-1,3-diketo-trans-decahydroisoquinoline

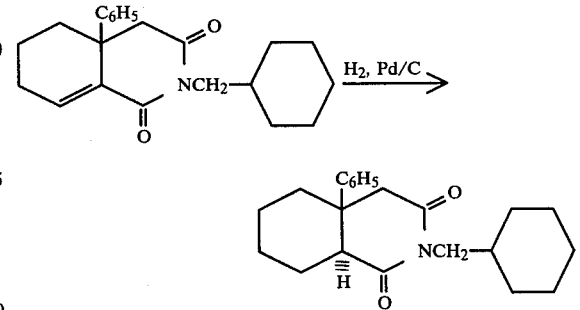

A mixture of the product of Part A (858 mg), 75 ml of glacial acetic acid and 200 mg of 5% palladium on carbon was shaken under 40 psi of hydrogen for 24 hours. The catalyst was removed by filtration and the solvent evaporated to yield crude N-cyclohexylmethylimide.

IR: 5,80 and 5.96μ (imide C=O); 6.25, 6.35μ (Ar C=C).

C.
N-Cyclohexylmethyl-4a-phenyl-trans-decahydroisoquinoline

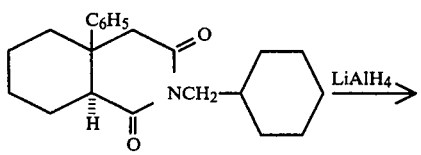

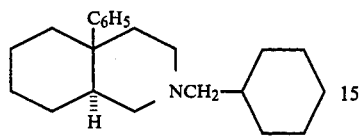

The crude product from Part B was taken up in 50 ml of anhydrous tetrahydrofuran, lithium aluminum hydride (860 mg) was added and the mixture refluxed, under nitrogen, overnight. It was allowed to cool, then was treated successively with 0.9 ml of water, 0.9 ml of 15% aqueous sodium hydroxide and 2.7 ml of water. The precipitated inorganic salts were filtered off and washed well with ether. The combined filtrates were dried over anhydrous potassium carbonate, concentrated, and the residual oil distilled, bp 110° (0.004 mm). The product was identified as N-cyclohexylmethyl-4a-phenyl-trans-decahydroisoquinoline.

Anal. Calcd for $C_{22}H_{33}N$: C, 84.83; H, 10.68; N, 4.50. Found: C, 84.85; H, 10.03; N, 4.74.

EXAMPLE 7
N-Phenethyl-4a-(m-methoxyphenyl)-trans-decahydroisoquinoline

A.
N-Phenethyl-4a-(m-methoxyphenyl)-1,3-diketo-1,2,3,4,4a,5,6,7-octahydroisoquinoline

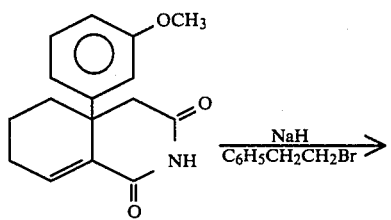

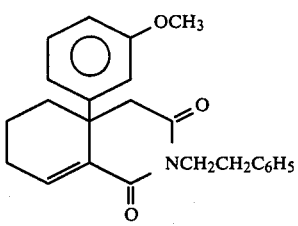

A solution of 4a-(m-methoxyphenyl)-1,3-diketo-1,2,3,4,4a,5,6,7-octahydroisoquinoline (2.2 g, 8.12 mmoles) in 15 ml of dry dimethylformamide was added dropwise to 386 mg of a 55% suspension of sodium hydride in mineral oil in 15 ml of dimethylformamide at 70° C. The reaction mixture was heated at 70° C. for 1 hour then cooled to 0° C. and 1.65 g of phenethyl bromide in 15 ml of dimethylformamide was added. The mixture was stirred at 25° for 65 hours then poured into water and extracted with ether to yield, after trituration with ethanol, 2.32 g of N-phenethyl-4a-(m-methoxyphenyl)-1,3-diketo-1,2,3,4,4a,5,6,7-octahydroisoquinoline, mp 134°–135°.

Anal. Calcd for $C_{24}H_{25}NO_3$: C, 76.76; H, 6.71; N, 3.73.

| Found: | C, 75.94; | H, 6.60; | N, 3.73 |
|---|---|---|---|
| | 75.97 | 6.53 | 3.72. |

B.
N-Phenethyl-4a-(m-methoxyphenyl)-1,3-diketo-trans-decahydroisoquinoline

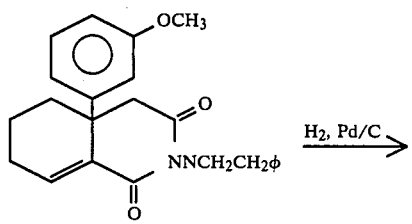

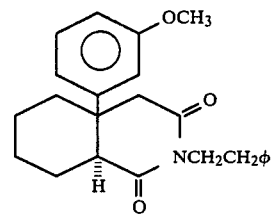

A mixture of the product of Part A (2.3 g), 100 ml of glacial acetic acid and 600 mg of 5% palladium on carbon was shaken under 40 psi of hydrogen for 18 hours. The catalyst was filtered off and the filtrate was concentrated to yield a crystalline solid, mp, 119°–122° C., identified as N-phenethyl-4a-(m-methoxyphenyl)-1,3-diketo-trans-decahydroisoquinoline.

C.
N-Phenethyl-4a-(m-methoxyphenyl)-trans-decahydroisoquinoline

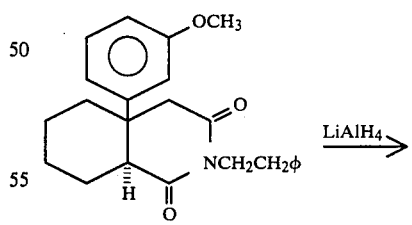

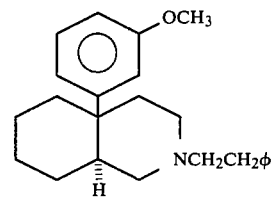

The product from Part B was taken up in 100 ml of dry di(ethylene glycol) dimethyl ether, 2.64 g of lithium aluminum hydride was added and the mixture heated at 110°–120° C. for 48 hours. It was cooled to 0° C. then treated successively with 3.0 ml of water, 3.0 ml of 15% aqueous sodium hydroxide, and finally 9.0 ml of water. The inorganic salts were filtered and the filtrate evaporated. The residue was taken up in ether, dried (K$_2$CO$_3$) and the solvent evaporated. The residue was evaporatively distilled, bp, 180° C. (0.004 mm), yielding 1.6 g of N-phenethyl-4a(m-methoxyphenyl)-trans-decahydroisoquinoline.

NMR (COCl$_3$): methylene envelope over 40–180 cps from TMS; singlet at 227 cps (OCH$_3$); complex multiplet centered at 431 cps (ArH).

Anal. Calcd for C$_{24}$H$_{31}$NO: C, 82.47; H, 8.94; N, 4.00. Found: C, 81.92; H, 8.99; N, 3.75.

EXAMPLE 8

N-Phenethyl-4a-(m-hydroxyphenyl)-trans-decahydroisoquinoline

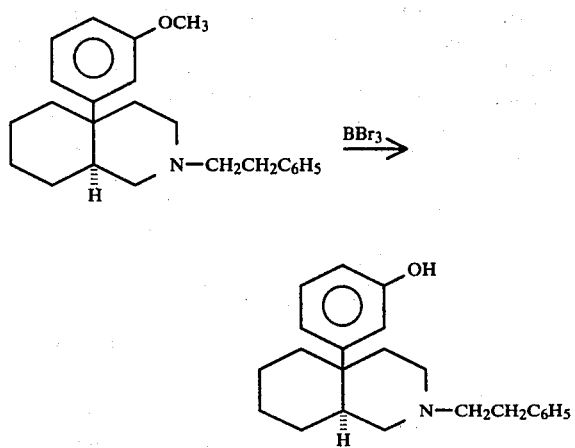

A solution of 1.25 g (3.58 mmoles) of the product from Example 7, Part C, in 30 ml of methylene chloride was added over 20 minutes to a solution of 0.7 ml of boron tribromide (7.2 mmoles) in 15 ml of methylene chloride at 0° C. The mixture was stirred at 0° C. for 2 hours then at 25° C. overnight. The reaction was worked up as outlined in Example 4, to yield after evaporative distillation an oil, bp 220° C. (0.003 mm), which was triturated with ether to give a crystalline solid, mp, 184°–190°, identified as N-phenethyl-4a-(m-hydroxyphenyl)-trans-decahydroisoquinoline.

NMR (CDCl$_3$): Absence of singlet at 227 cps (OCH$_3$) present in product from Part C of Example 7 indicated the methyl ether had been demethylated.

EXAMPLE 9

N-Cyclopropylmethyl-4a-(m-methoxyphenyl)-trans-decahydroisoquinoline

A.

N-Cyclopropylmethyl-4a-(m-methoxyphenyl)-1,3-diketo-1,2,3,4,4a,5,6,7-octahydroisoquinoline

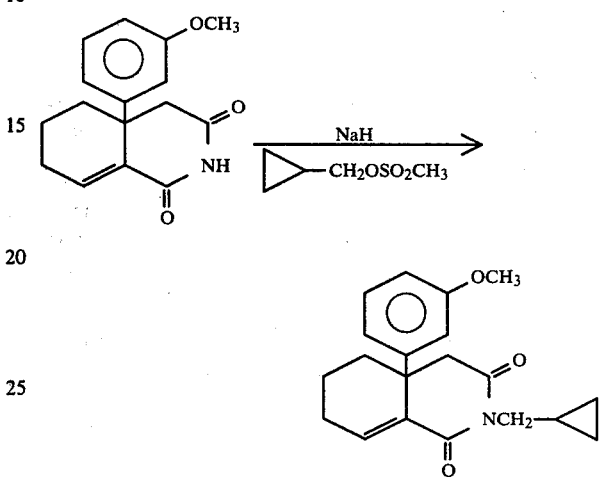

4a-(m-Methoxyphenyl)-1,3-diketo-1,2,3,4,4a,5,6, 7-octahydroisoquinoline (99 g, 0.365 moles) in 1000 ml of anhydrous dimethylformamide was added dropwise to a 55% suspension of sodium hydride in mineral oil (19.8 g) in 500 ml of dimethylformamide at 70°. The reaction mixture was heated for 1 hour at 80° and then cooled to 25°. Cyclopropylmethylmesylate (59.6 g) was added and the reaction mixture heated at 70°–80° for one hour and stirred overnight. It was poured into water and extracted with ether. The residue after evaporation of the ether was chromatographed on 800 g of Florisil. The final product, after evaporative distillation at 190° (1μ), amounted to 50 g.

IR (neat): 5.83, 6.0μ (imide C═O's); 6.11μ (C═C); 6.25, 6.35μ (Ar)

NMR (CDCl$_3$): multiplets from 0–20 cps (Δ); multiplets from 40–150 cps (—CH$_2$'s); AB quartet at 152, 168, 195, 210 cps (CH$_2$—CO, 2H); doublet at 209, 216 cps (N—CH$_2$—<, 2H); singlet at 226 cps (OCH$_3$, 3H); multiplets at 397–440 cps (ArH, 4H); triplet at 441, 445, 449 cps (═CH, 1H).

B.

N-Cyclopropylmethyl-4a-(m-methoxyphenyl)-1,3-diketo-trans-decahydroisoquinoline

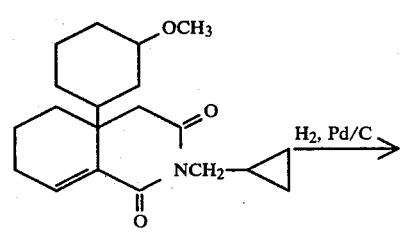

The procedure in Example 9, Part A was followed in which 4a-(m-methoxyphenyl)-1,3-diketo-1,2,3,4,4a,5,6,7-octahydroisoquinoline (10.74 g) in 135 ml of anhydrous dimethylformamide was added to a 55% suspension of sodium hydride in mineral oil (2.15 g) in 90 ml of dimethylformamide at 70° C. Cyclobutylmethylmesylate (9 g) was added and the reaction heated at 80°-90° C. for 6 hours, then at 25° C. for 10 hours. This gave, after chromatography, a crystalline product (6 g), mp 89°-93° C.

Anal. Calcd for $C_{21}H_{25}NO_3$: C, 74.31; H, 7.42; N, 4.12. Found: C, 73.88; H, 8.03; N, 3.94.

IR (neat); 5.81, 6.0μ (imide CO's); 610μ (C=C); 6.25, 6.35μ (Ar).

NMR (CDCl$_3$): multiplets at 50 to 150 cps (—CH$_2$'s); quartet at 151, 167, 197, 212 cps (CH$_2$—CO); doublet at 220, 226 (NCH$_2$—<); singlet at 226 cps (OCH$_3$); multiplets at 400–440 (ArH); triplet at 441, 445, 449 (C=CH).

B.
N-Cyclobutylmethyl-4a-(m-methoxyphenyl)-1,3-diketo-trans-decahydroisoquinoline

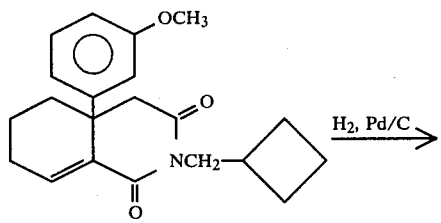
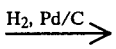

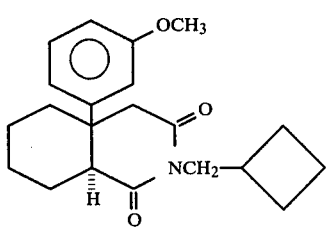

The product from Part A (6 g) was reacted as in Example 9, Part B with 100 ml of absolute ethanol, 2 g of 5% palladium on carbon and 40 psi of hydrogen to give N-cyclobutylmethylimide, mp, 70°-74° (from ethanol).

Anal. Calcd for $C_{21}H_{27}NO_3$: C, 73.87; H, 7.97; N, 4.10. Found: C, 73.59; H, 8.04; N, 3.78.

C. N-Cyclobutylmethyl-4a-(m-methoxyphenyl)-trans-decahydroisoquinoline

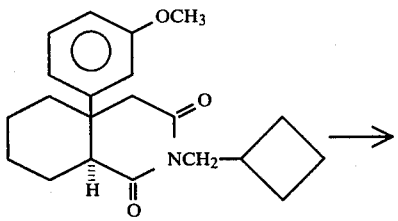

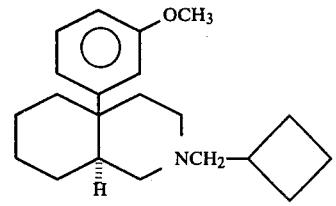

The product from part B (4.6 g) was reacted as in Example 9, Part C, with 150 ml of anhydrous tetrahydrofuran and 5 g of lithium aluminum hydride at reflux for 24 hours. This gave after evaporative distillation at 155° (0.07 mm), N-cyclobutylmethyl-4a-(m-methoxyphenyl)-trans-decahydroisoquinoline.

Anal. Calcd for $C_{21}H_{31}NO$: C, 80.46; H, 9.97; N, 4.47. Found: C, 79.74; H, 9.69; N, 4.38.

HRMS: Calcd for $C_{21}H_{31}NO$: 313.2404. Found: 313.2371.

NMR (CDCl$_3$): multiplets at 60 to 180 cps (CH$_2$'s); singlet at 226 cps (OCH$_3$); multiplets at 390–440 cps (ArH)

EXAMPLE 12
N-Cyclobutylmethyl-4a-(m-hydroxyphenyl)-trans-decahydroisoquinoline

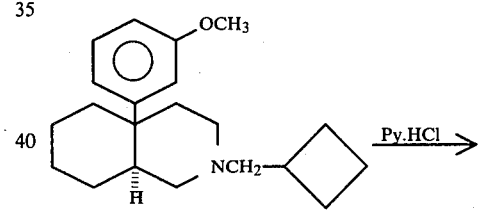

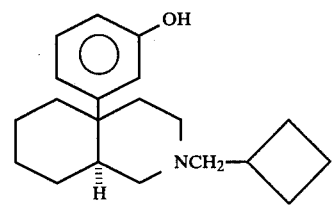

A mixture of the product from Example 11 (1.2 g) and pyridine hydrochloride (5 g) was heated at 210° for 1 hour, then cooled, diluted with water, and extracted with ether. The aqueous fraction was basified with solid potassium carbonate and extracted with ether. Evaporation of the solvent gave a residue which was evaporatively distilled at 240° (1μ).

Anal. Calcd for $C_{20}H_{29}NO$: C, 80.21; H, 9.76; N, 4.68. Found: C, 79.99; H, 10.10; N, 4.86.

NMR (CDCl$_3$): multiplets from 50–180 cps (CH$_2$'s, 24 H); multiplets at 388–440 cps (ArH, 4H); singlet at 520 cps (OH, 1H)

EXAMPLE 13

N-(n-Pentyl)-4a-(m-methoxyphenyl)-trans-decahydroisoquinoline

A.

N-(n-Pentyl)-4a-(m-methoxyphenyl)-1,3-diketo-1,2,3,4,4a,5,6,7-octahydroisoquinoline

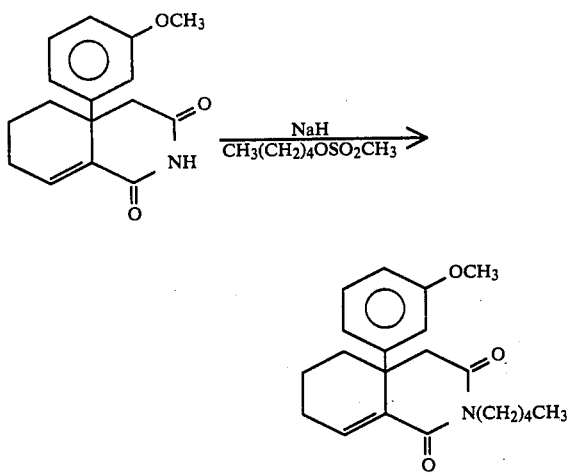

The procedure in Example 9, Part A, was followed in which 4a-(m-methoxyphenyl)-1,3-diketo-1,2,3,4,4a,5,6,7-octahydroisoquinoline (12 g, 0.0443 moles) in 150 ml of anhydrous dimethylformamide was added to a 55% suspension of sodium hydride in mineral oil (2.4 g, 0.055 moles NaH) in 100 ml of dimethylformamide at 70°; n-pentyl bromide (8.3 g, 0.055 moles) was added and the mixture heated at 70° for 3 hours, then allowed to stand 18 hours at 25°. Workup after chromatography of Florisil gave 12.5 g of a clear oil; one spot on thin-layer chromatograph (silica gel, 16% ether-benzene).

IR: 5.81, 6.0μ (imide carbonyls); 6.1μ (C=C); 6.25, 6.34μ (Ar).

NMR (CDCl$_3$): multiplets from 35–140 cps (CH$_2$'s); quartet at 149, 164, 193, 210 cps (CH$_2$CO, 2H); triplet at 202, 210, 217 cps (NCH$_2$—) and singlet at 224 cps (OCH$_3$) (5H); multiplets at 395–435 cps (ArH, 4H); triplet at 437, 440, 444 cps (=CH, 1H).

B.

N-(n-Pentyl)-4a-(m-methoxyphenyl)-1,3-diketo-trans-decahydroisoquinoline

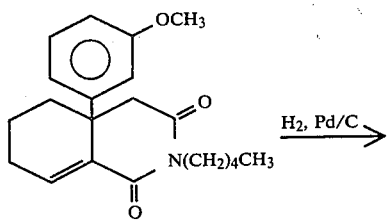

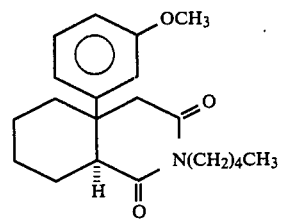

The product from Part A (12 g) was reacted as in Example 9, Part B, with 100 ml of absolute ethanol, 4 g of 5% palladium on carbon and 40 psi of hydrogen for 18 hours to give 12 g of product.

IR (neat): 5.80, 6.0μ (imide C=O's); 6.25, 6.32μ (ArH).

NMR (CDCl$_3$): multiplets at 40–150 cps (CH$_2$'s); quartet at 148, 164, 174, 191 cps (CH$_2$CO, 2H); singlet at 223 cps (OCH$_3$) and triplet at 210, 216, 22 cps (NCH$_2$) (5H); multiplets at 395–435 cps (ArH, 4H).

C.

N-(n-Pentyl)-4-a-(m-methoxyphenyl)-trans-decahydroisoquinoline

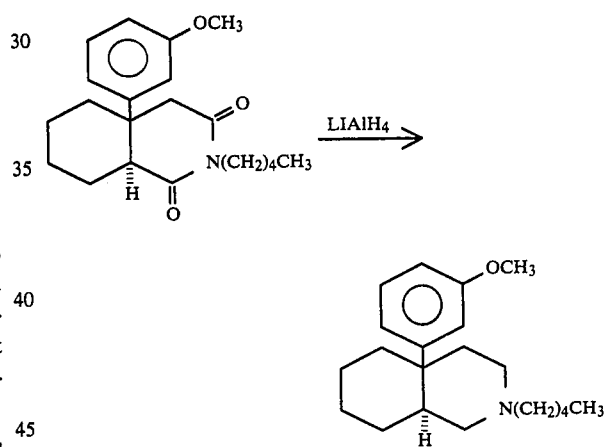

The product from Part B (12 g) was reacted as in Example 9, Part C, with 250 ml of anhydrous tetrahydrofuran and 12 g of lithium aluminum hydride at reflux for 18 hours. This gave an oil which was evaporatively distilled at 210° (20μ), to give 8 g of product.

IR (neat): 6.25, 6.33μ (Ar).

EXAMPLE 4

N-(n-Pentyl)-4a-(m-hydroxyphenyl)-trans-decahydroisoquinoline

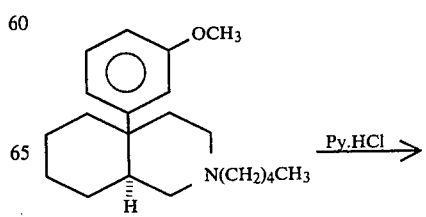

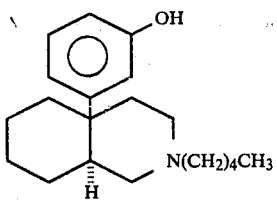

A mixture of the product from Example 13 (8 g) and pyridine hydrochloride (32 g) was heated to 210°, under nitrogen, for 90 minutes. The mixture was cooled, diluted with 150 ml of water and extracted with 150 ml of methylene chloride. The residue from the evaporated organic extracts was mixed with 150 ml of water and solid potassium carbonate until basic and then extracted with methylene chloride.

The residue from evaporation of the methylene chloride was evaporatively distilled at 230° (10μ) to yield 4 g of product.

Anal. Calcd for $C_{20}H_{31}NO$: C, 79.67; H, 10.37; N, 4.65. Found: C, 79.92; H, 10.40; N, 4.93.

NMR (CDCl$_3$): multiplets from 40–180 cps (CH$_2$'s, 26H); multiplets at 387–435 cps (ArH, 4H); singlet at 540 cps (OH, 1H).

EXAMPLE 15

N-(n-Hexyl)-4a-(m-methoxyphenyl)-trans-decahydroisoquinoline

A.

N-(n-Hexyl)-4a-(m-methoxyphenyl)-1,3-diketo-1,2,3,4,4a,5,6,7-octahydroisoquinoline

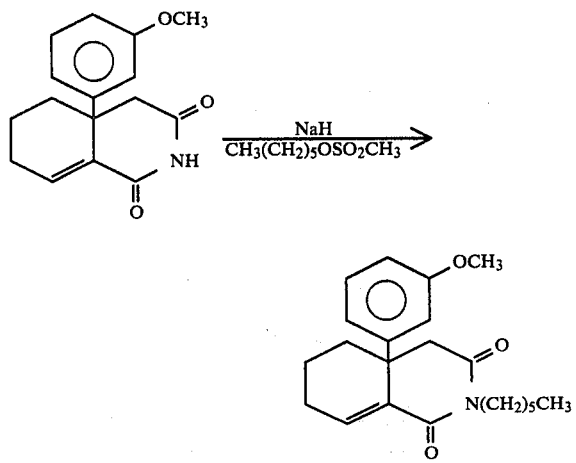

The procedure in Example 9, Part A, was followed in which 4a-(m-methoxyphenyl)-1,3-diketo-1,2,3,4,4a,5,6,7-octahydroisoquinoline (12 g, 0.05 moles) in 150 ml of anhydrous dimethylformamide was added to a 55% suspension of sodium hydride in mineral oil (2.4 g) in 100 ml of dimethylformamide at 70°; n-hexyl bromide (9.1 g) was added, the reaction heated at 70° for 18 hrs. The crude material obtained from this procedure was chromatographed to yield 12 g of product.

IR (neat): 5.80, 5.98μ (imide C=O's); 6.10μ (C=C); 6.25, 6.35μ (Ar).

NMR (CDCl$_3$): multiplet from 40–145 cps (CH$_2$'s); quartet at 148, 164, 193, 208 cps (CH$_2$CO, 2H); triplet at 204, 209, 216 cps (NCH$_2$—) and singlet at 224 cps (OCH$_3$) (5H); multiplets from 395–430 cps (ArH, 4H); triplet at 437, 441, 444 cps (=CH, 1H).

B.

N-(n-Hexyl)-4a-(m-methoxyphenyl)-1,3-diketo-trans-decahydroisoquinoline

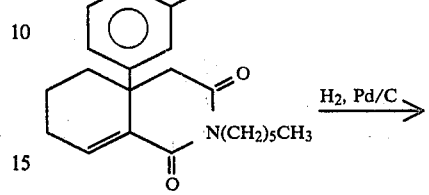

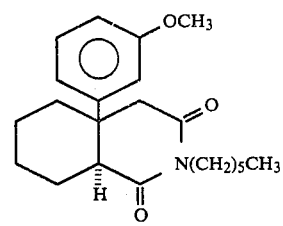

The product from Part A (12 g) was reacted as in Example 9, Part B, with 100 ml of absolute ethanol, 4 g of 5% palladium on carbon and 40 psi of hydrogen to give crude N-(n-hexyl)-imide.

IR (neat): 5.83; 6.0μ (imide C=O's); 6.25, 6.35μ (Ar).

NMR (CDCl$_3$): multiplets from 40–145 cps (—CH$_2$'s); 150, 177, 194 cps (CH$_2$CO); singlet at 226 cps (OCH$_3$) and multiplet at 210–231 (N—CH$_2$); multiplets at 400–440 cps (ArH).

C.

N-(n-Hexyl)-4a-(m-methoxyphenyl)-trans-decahydroisoquinoline

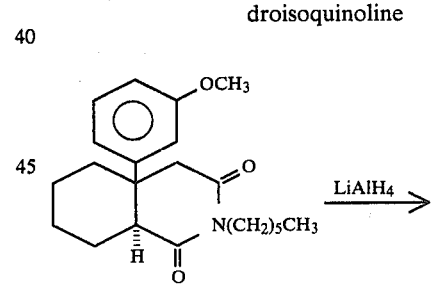

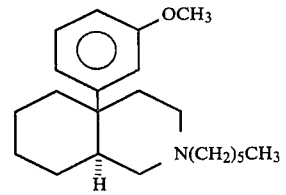

The product from Part B (12 g) was reacted as in Example 9, Part C, with 250 ml of anhydrous tetrahydrofuran and 12 g of lithium aluminum hydride for 18 hours at reflux. This gave, after evaporative distillation at 230° (5μ), 9 g of product.

EXAMPLE 16

N-(n-Hexyl)-4a-(m-hydroxyphenyl)-trans-decahydroisoquinoline

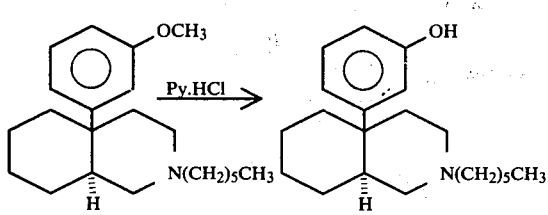

A mixture of the product from Example 15 (9 g) and pyridine hydrochloride (36 g) was heated to 210°, under nitrogen for 90 minutes. The product was worked up as indicated in Example 14 to give, after evaporative distillation at 230° (4μ), 9 g of product. This material was crystallized from ethanol; mp 150°–152°.

Anal. Calcd for C$_{21}$H$_{33}$NO: C, 79.94; H, 10.54; N, 4.44. Found: C, 79.72; H, 10.64; N, 4.74.

NMR (CDCl$_3$): multiplets from 40–175 cps (CH$_2$'s); multiplet from 390–440 cps (ArH).

EXAMPLE 17

N-Cyclopropylmethyl-4a-phenyl-trans-decahydroisoquinoline

A.

N-Cyclopropylmethyl-4a-phenyl-1,3-diketo-1,2,3,4,4a,5,6,7-octahydroisoquinoline

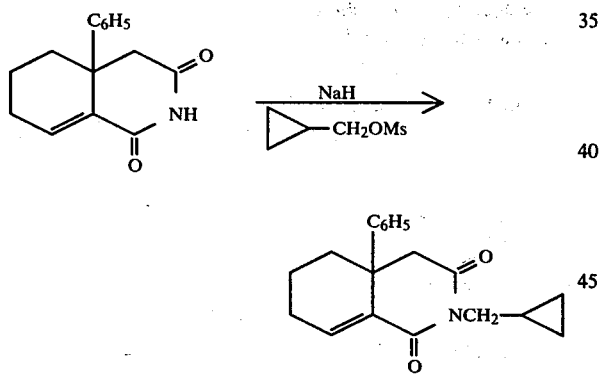

A solution of 4a-(phenyl)-1,3-diketo-2,3,4,4a,5,6,7-octahydroisoquinoline (10.0 g. 0.0415 mole) in 75 ml of dry dimethylformamide was added dropwise to 1.97 g of 55% suspension of sodium hydride in mineral oil in 50 ml of dimethylformamide at 80°. The reaction mixture was heated for 1 hour at 80° then cooled to 25°. Cyclopropylmethylmesylate (8.2 g) was added and the mixture heated at 70° C. for 1 hour then allowed to stir overnight at 25°. It was poured into water and extracted with ether. The residue after evaporation of the ether was chromatographed on 350 g of Florisil and eluted with acetone-hexane mixtures to yield 8 g mp, 71°–71.7° C.

Anal. calcd for C$_{19}$H$_{21}$NO$_2$: C, 77.26; H, 7.17; N, 4.74. Found: C, 76,78; H, 7.15; N, 4.57.

B.

N-Cyclopropylmethyl-4a-phenyl-1,3-diketo-trans-decahydroisoquinoline

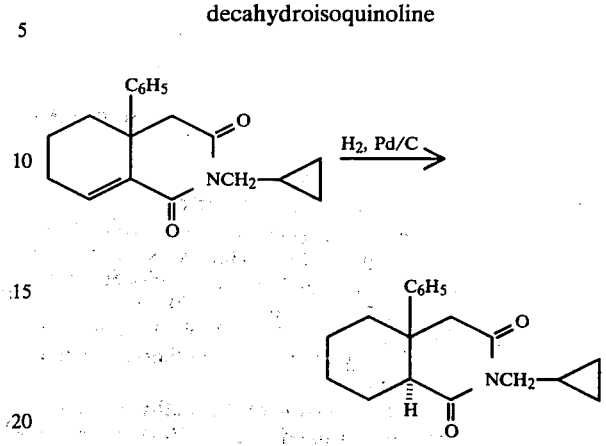

A mixture of the product from Part A (6 g), 100 ml of absolute ethanol and 5% palladium on carbon (2 g) was shaken under 40 psi of hydrogen for 24 hours. The catalyst was removed by filtration and the solvent evaporated to yield crude N-cyclopropylmethylimide.

IR (neat): 5.80, 5.95μ (imide C=O's); 6.25, 6.35μ (Ar).

C.

N-Cyclopropylmethyl-4a-phenyl-trans-decahydroisoquinoline

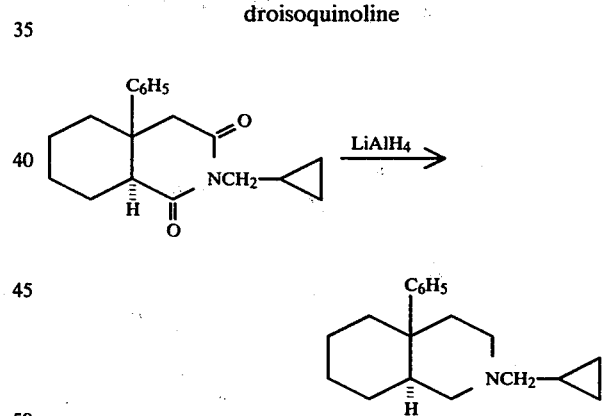

The crude product from Part B (6 g) was taken up in 200 ml of anhydrous tetrahydrofuran, lithium aluminum hydride (6 g) was added, and the mixture refluxed under nitrogen overnight. It was allowed to cool then treated successively with 6 ml of water, 6 ml of 15% aqueous sodium hydroxide and 18 18 ml. of water. The precipitated inorganic salts were filtered off and washed well with ether. The combined filtrates were dried over anhydrous potassium carbonate, concentrated, and the residual oil distilled, bp, 120° (2μ). The product was identified as N-cyclopropylmethyl-4a-phenyl-trans-decahydroisoquinoline.

Anal. Calcd for C$_{19}$H$_{27}$N: C, 84.70; H, 10.10; N, 5.20. Found: C, 84.36; H, 10.05; N, 5.65.

EXAMPLE 18

N-Cyclopropylmethyl-4a-(m-methoxyphenyl)-6-methyl-trans-decahydroisoquinoline

A. 2-(m-Methoxyphenyl)-4-methyl-cyclohexanone

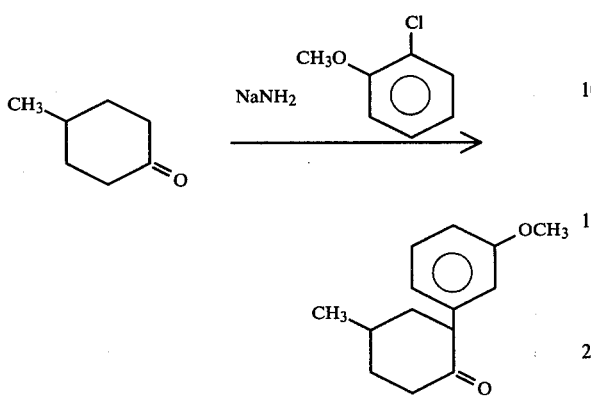

Employing the general procedure of T. Kametani, et al., J. Chem. Soc. (C), 1971, 1047, 187 g o-chloroanisole was added to a mixture of 215 g of sodium amide, 3 liters of anhydrous tetrahydrofuran and 400 g of 4-methylcyclohexanone. The reaction was refluxed for 18 hours then quenched with saturated ammonium chloride. Concentration of the organic phase, dilution with water, extraction with ether and distillation of the residue from concentrating the ether extracts gave 90 g, b.p. 135° (0.07 mm), of product.

B.
2-(m-Methoxyphenyl)-4-methyl-2-carbethoxycyclohexanone

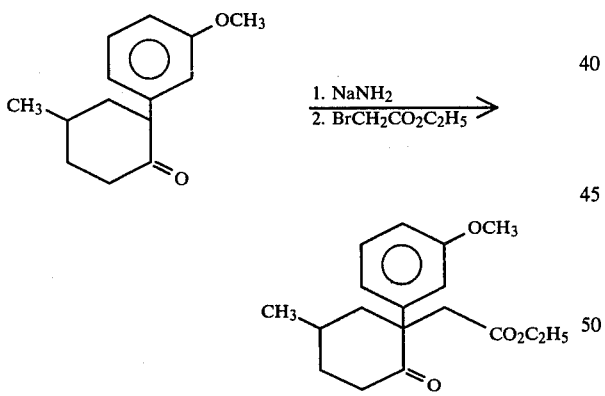

The product from Part A (87 g) in 125 ml of anhydrous ether and 75 ml of anhydrous benzene was added to 17.1 g of sodium amide in 200 ml of ether. The mixture was refluxed for 4 hours. It was then cooled in an ice-salt bath to 0° and 80 g of ethyl bromoacetate was added over 45 minutes. The reaction was stirred overnight at 25° then cooled in ice, treated with aqueous ammonium chloride, then water. Extraction with ether and distillation of the residue from concentration of the ether extracts gave a viscous oil, b.p. 160° (0.07 mm), yield 60 g. A portion of this material (54 g) in 150 ml of ethanol was treated with 34.2 g of potassium hydroxide, 9 ml of water, and 150 ml of ethanol and refluxed for 4 hours. The reaction was cooled and concentrated on a rotary evaporator under vacuum. Water was added. The aqueous solution was extracted with ether. The aqueous portion was basified with solid potassium hydroxide and extracted with ether. Concentration of these ether extracts gave a residue [2-(m-methoxyphenyl)-2-carboxymethyl-4-methylcyclohexanone] which was re-esterified with ethanol and a few drops of sulfuric acid, to give, after evaporation of the solvent and distillation, 30 g, b.p. 140° (0.07 mm), of product.

C.
2-Cyano-3-(m-methoxyphenyl)-3-carbethoxymethyl-5-methylcyclohexene

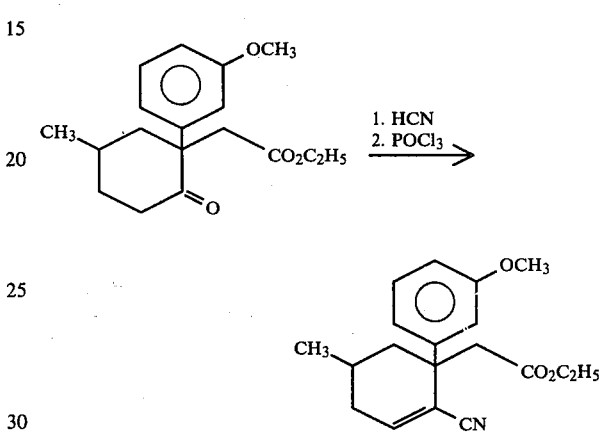

The product from Part B (25 g) was reacted with 200 ml of hydrogen cyanide as described in Example 1, Part A. Subsequent treatment of the cyanohydrin with 200 ml anhydrous pyridine and 25 ml of phosphorus oxychloride (see Example 1, Part A) gave, after distillation at 160° (0.07 mm), 15 g of product.

D.
4a-(m-Methoxyphenyl)-6-methyl-1,3-diketo-1,2,3,4,4a,5,6,7-octahydroisoquinoline

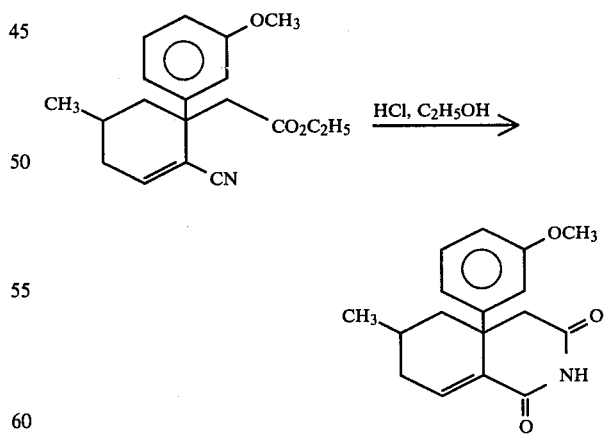

The product from Part C (12 g) was reacted as in Example 1, Part B, with a solution of ethanol (250 ml) saturated with anhydrous hydrogen chloride to give 4.7 g, m.p. 218°–221°.

Anal. Calcd for $C_{17}H_{19}NO_3$: C, 71.56; H, 6.71; N, 4.91. Found: C, 71.58; H, 6.69; N, 4.95.

E.
N-Cyclopropylmethyl-4a-(m-methoxyphenyl)-6-methyl-1,3-diketo-1,2,3,4,4a,5,6,7-octahydroisoquinoline

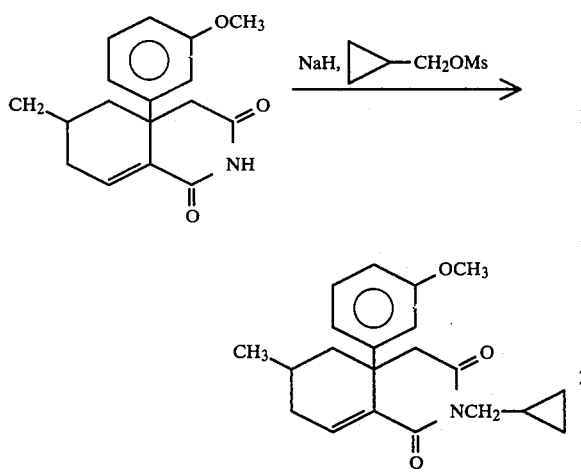

The product from Part D (3.14 g) in 50 ml of anhydrous dimethylformamide was reacted as in Example 1, Part C, with 0.6 g of a 55.5% suspension of sodium hydride in mineral oil in 50 ml of dimethylformamide. Subsequent treatment with 2.5 g of cyclopropylmethyl mesylate and isolation gave, after chromatography on 180 g of Florisil and elution with acetonehexane fractions, 3 g of product (clear oil).

IR (neat): 5.75, 5.95μ (imide C=O's); 6.03μ (C=C); 6.25, 6.35μ (Ar).

NMR (CDCl₃): doublet at 65, 69 cps (6CH₃, 3H); multiplets at 5–20 cps (Δ, 5H); multiplets at 80–160 cps (CH₂'s, 5H); AB quartet at 176, 192, 201, 218 cps (CH₂CO, 2H); doublet at 216, 222 cps (NCH₂ 2H); singlet at 235 cps (OCH₃ 3H); multiplets at 405–450 cps (=CH, ArH, 5H).

F.
N-Cyclopropylmethyl-4a-(m-methoxyphenyl)-6-methyl-1,3-diketo-trans-decahydroisoquinoline

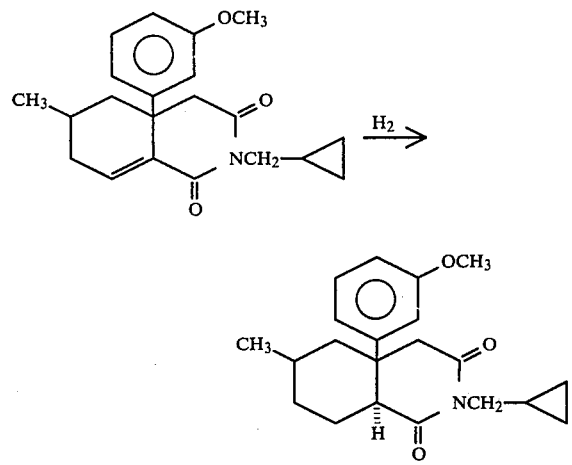

The product from Part E (3 g) was reacted as in Example 9, Part B, with 150 ml of ethanol, 1 g of 5% palladium on carbon and 40 psi of hydrogen to give the N-cyclopropylmethyl-4a-(m-methoxyphenyl)-6-methylimide, 3 g.

IR: 5.85, 5.97μ (imide C=O's); 6.25, 6.35μ (C=C).

G.
N-cyclopropylmethyl-4a-(m-methoxyphenyl)-6-methyl-trans-decahydroisoquinoline

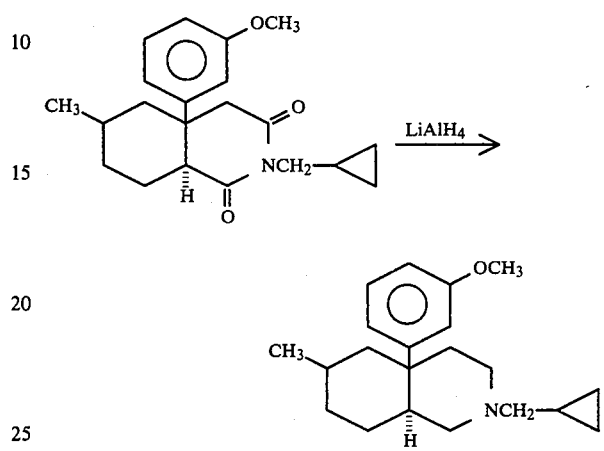

The product from Part F (3 g) was reacted as in Example 9, Part C, with 100 ml of anhydrous tetrahydrofuran and 3 g of lithium aluminum hydride at reflux for 24 hours to give, after evaporative distillation at 135° (1μ), 1.3 g of product.

Anal. calcd for $C_{21}H_3$, NO: C, 80.46; H, 9.97, N, 4.47. Found: C, 80.17; H, 10.00; N 4.11.

EXAMPLE 19
N-Cyclopropylmethyl-4a-(m-hydroxyphenyl)-6-methyl-trans-decahydroisoquinoline

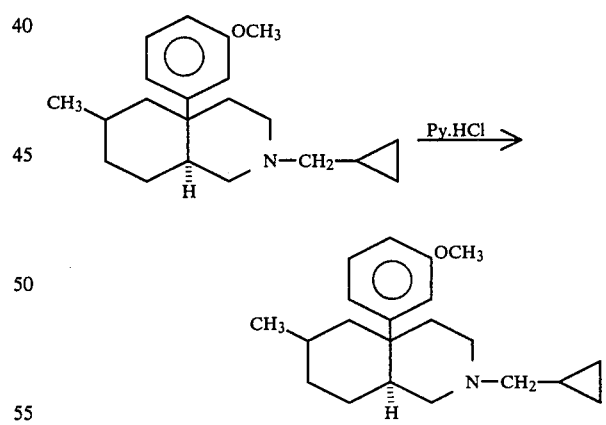

A mixture of the product of Example 18 (0.5 g) and pyridine hydrochloride (2 ) was heated to 210° under nitrogen for 90 minutes. The resulting product was worked up as in Example 14 to give, after evaporative distillation, the above-titled compound.

The novel 4a-aryl-trans-decahydroisoquinolines of formula I are generally useful as analgesics which can be administered by any means that effects contact of the compound with the site of action in the body of a warm-blooded animal. Such means include parenteral (i.e., subcutaneously, intravenously, intramuscularly or intraperitoneally) and oral (alternatively or concurrently with parenteral) administration. The analgesic activity of these compounds is evidenced by the results, shown in the following examples, of tests conducted with female white mice.

EXAMPLE A

In a standard mouse test modified from Siegmund et al. [Proc. Soc. Exp. Biol. Med. 95, 729 (1957)], a test compound suspended in 1% Methocel ® was given orally to fasted (17-21 hours) female white mice, 5-20 animals per double blind test. Aqueous (0.01%) phenyl-p-benzoquinone (phenylquinone) was injected intraperitoneally at 23 or 30 minutes later using 0.25 ml per mouse. Commencing at 30 or 37 minutes, respectively, after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Weil [Biometrics 8, 249 (1952)]. The oral $ED_{50}$ dosages of several compounds of the invention are:

| Compound | $ED_{50}$ (mg/kg) |
|---|---|
| Example 3-E | 3 |
| Example 4 | 2.3 |
| Example 9 | 8 |

Some of the compounds appear to be nonaddicting analgesics as evidenced by the fact they do not produce the Straub tail in mice [I. Shemano and H. Wendel, Toxicology and Applied Pharmacology 6, 334 (1964) and references cited therein]. Included in this group are the compounds of examples 9, 10, 16 and 18.

EXAMPLE B

The optical isomers of N-methyl-4a-phenyl-trans-decahydroisoquinoline (products of Example 2H, parts 1 and 2) were tested for analgesic activity by the phenylquinone writhing test described in Example A. The following table shows that both the dextro and laevo forms are active, the dextro form being significantly more effective than the laevo form.

| Isomer | $ED_{50}$ (mg/kg) |
|---|---|
| Dextro (Ex. 2H-2) | 3.5 |
| Laevo (Ex. 2H-1) | 23.0 |

The other novel products of this invention are the 1,3-diketo compounds of formulas 2, 3, 4 and 5 which are all useful as chemical intermediates to the new analgesics of the invention.

The embodiments of the invention in which an exclusive property or privilege is claimed are defined as follows:

1. A compound of the formula

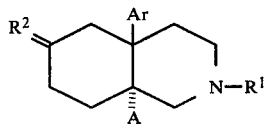

wherein $R^1$ is $C_1-C_6$ alkyl or cycloalkylmethyl of the formula
—$CH_2OH<(CH_2)_n$ in which n is an integer in the range 2-5;

$R^2$ is

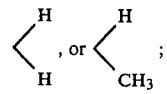

A is hydrogen or hydroxyl;

Ar is

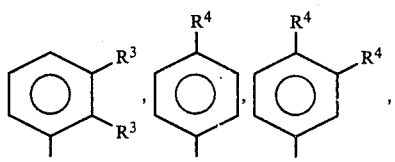

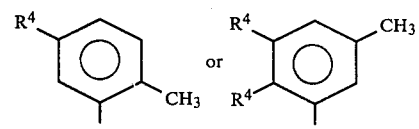

in which $R^3$ is hydrogen, hydroxyl, methoxyl or acetoxyl;

$R^4$ is hydroxyl, methoxyl or acetoxyl; and jointly, two of $R^3$ or of $R^4$ situated on adjacent carbons may be combined to form a divalent methylenedioxy (—OCH$_2$O—) group; provided that when $R^1$=methyl, $R^3$ may not both be hydrogen.

2. A compound according to claim 1 which is dextrorotatory.

3. A compound according to claim 1 which is laevorotatory.

4. The compound N-methyl-4a(m-methoxyphenyl)-trans-decahydroisoquinoline.

5. The compound N-methyl-4a-(m-hydroxyphenyl)-trans-decahydroisoquinoline.

6. The compound N-methyl-4a-phenyl-8a-hydroxy-trans-decahydroisoquinoline.

7. The compound of claim 1 which is N-cyclohexylmethyl-4a-phenyl-trans-decahydroisoquinoline.

8. The compound of claim 1 which is N-cyclopropylmethyl-4a-(m-methoxyphenyl)-trans-decahydroisoquinoline.

9. The compound of claim 1 which is N-cyclopropylmethyl-4a-(m-hydroxyphenyl)-trans-decahydroisoquinoline.

10. The compound of claim 1 which is N-(n-hexyl)-4a-(m-hydroxyphenyl)-trans-decahydroisoquinoline.

11. The compound of claim 1 which is N-cyclopropylmethyl-4a-(m-methoxyphenyl)-6-methyl-trans-decahydroisoquinoline.

12. The compound of claim 1 which is N-cyclopropylmethyl-4a-(m-hydroxyphenyl)-6-methyl-trans-decahydroisoquinoline.

13. A compound of the formula

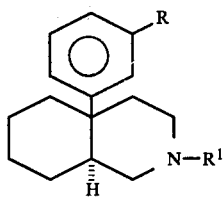

in which

R is —OH or —OCH₃; and

R¹ is alkyl of 1-6 carbon atoms; inclusive, or a pharmaceutically suitable salt thereof.

14. A compound of the formula

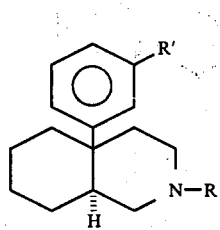

wherein

R is cyclopropylmethyl or cyclobutylmethyl;

R¹ is hydroxyl, methoxyl or acetoxyl; and pharmaceutically-acceptable acid addition salts thereof.

15. A compound according to claim 14 in which R' is OH.

16. A compound according to claim 14 in which R¹ is methoxyl.

17. A compound according to claim 14 in which R is cyclopropylmethyl.

18. A compound according to claim 14, said compound being trans-dl-1-cyclobutylmethyl-3a-(m-hydroxyphenyl)-1,2,3,3a,4,5,6,7a,8-decahydroisoquinoline.

19. A compound according to claim 14, said compound being trans-dl-1-cyclopropylmethyl-3a(m-hydroxyphenyl)-1,2,3,3a,4,5,6,7,7a,8-decahydroisoquinoline.

20. A compound according to claim 14, said compound being trans-1(—)-1-cyclopropylmethyl-3a-(m-hydroxyphenyl)-1,2,3,3a,4,5,6,7,7a,8-decahydroisoquinoline.

21. A trans-dl racemate of a compound according to claim 14.

22. A trans-dl racemate of a compound according to claim 14 in which R¹ is OH.

* * * * *